(12) United States Patent
Kamani et al.

(10) Patent No.: US 10,336,763 B1
(45) Date of Patent: Jul. 2, 2019

(54) CRYSTAL FORM B OF RIBOCICLIB SUCCINATE

(71) Applicant: Chunghwa Chemical Synthesis & Biotech Co. Ltd., New Taipei (TW)

(72) Inventors: Satyanarayana Kamani, New Taipei (TW); Tzu-Chiang Lu, New Taipei (TW); Hsin-Yun Chang, New Taipei (TW); Chin-Cheng Mai, New Taipei (TW)

(73) Assignee: CHUNGHWA CHEMICAL SYNTHESIS & BIOTECH CO. LTD., New Taipei (TW)

( * ) Notice: Subject to any disclaimer, the term of this patent is extended or adjusted under 35 U.S.C. 154(b) by 0 days.

(21) Appl. No.: 16/054,443

(22) Filed: Aug. 3, 2018

(30) Foreign Application Priority Data

May 17, 2018 (TW) .............................. 107116819 A

(51) Int. Cl.
*A61K 31/519* (2006.01)
*C07D 487/04* (2006.01)
*A61P 35/04* (2006.01)

(52) U.S. Cl.
CPC ............ *C07D 487/04* (2013.01); *A61P 35/04* (2018.01); *C07B 2200/13* (2013.01)

(58) Field of Classification Search
CPC ............................. A61K 31/519; C07D 487/04
USPC ......................................... 514/265.1; 544/280
See application file for complete search history.

(56) References Cited

FOREIGN PATENT DOCUMENTS

| | | |
|---|---|---|
| EP | 3156406 A1 | 4/2017 |
| WO | WO2012/064805 A1 | 5/2012 |

*Primary Examiner* — Douglas M Willis
(74) *Attorney, Agent, or Firm* — Muncy, Geissler, Olds & Lowe, P.C.

(57) ABSTRACT

The present invention relates to crystal forms B, C and D of Ribociclib succinate salt and derivatives thereof, and their preparation method and composition. The crystal forms B, C and D of Ribociclib succinate salts are obtained by adding 7-cyclopentyl-N,N-dimethyl-2-(5-(piperain-1-yl)pyridin-2-ylamino)-7H-pyrrolo[2,3-d]pyrimidine-6-carboxamide solution into succinic acid solution for reaction, stirring the solution under high temperature, filtering the solution after cooling off.

5 Claims, 17 Drawing Sheets

CRYSTAL FORM B OF RIBOCICLIB SUCCINATE

BACKGROUND OF THE INVENTION

1. Technical Field

The present invention relates to ribociclib succinates in crystalline forms B, C, and D; their derivatives; and preparation methods and pharmaceutical compositions thereof, wherein the pharmaceutical compositions can be used to treat advanced or metastatic breast cancer.

2. Description of Related Art

Ribociclib is an inhibitor of cyclin-dependent kinase (CDK) 4 and CDK6 and has the chemical name of 7-cyclopentyl-N,N-dimethyl-2-{[5-(piperazin-1-yl)pyridin-2-yl]amino}-7H-pyrrolo[2,3-d]pyrimidine-6-carboxamide. After the United States Food and Drug Administration (FDA) approved its New Drug Application in March 2017, ribociclib was introduced to the market, indicated primarily for treating breast cancer, such as advanced or metastatic hormone receptor (HR)-positive, human epithelial growth receptor-2 (HER-2)-negative mammary cancer in postmenopause women.

The most common compound salt type of ribociclib for pharmaceutical is ribociclib succinate salt, having chemical name of butanedioicacid-7-cyclopentyl-N,N-dimethyl-2-[(5-piperazin-1-ylpyridin-2-yl)amino]pyrrolo[2,3-D]pyrimidine-6-carboxamide.

Published PCT Patent Application No. WO 2012/064805A1 discloses a method for preparing a ribociclib succinate using palladium acetate (Pd(OAc)$_2$), which is an acetate of the costly rare noble metal palladium, as a catalyst. Published European Patent Application No. EP 3156406A1 discloses the crystalline forms of ribociclib free base and preparation methods thereof, the primary objective being to eliminate the health hazards associated with the use of excessive organic solvents in the conventional synthetic methods.

BRIEF SUMMARY OF THE INVENTION

However, the ribociclib succinate preparation method of WO 2012/064805A1 is disadvantageous to industrial production as it requires a costly noble-metal catalyst, i.e., palladium acetate (Pd(OAc)$_2$), and results in crystalline polymorphism in its products. Crystalline polymorphism in the active ingredient(s) of a pharmaceutical composition tends to compromise the storage stability, and hence efficacy, of the pharmaceutical composition.

As above, the objective of the present invention is a ribociclib succinate in crystalline form B, characterized by having characteristic peaks at 2θ values of 12.9°±0.20°, 13.7°±0.20°, 18.7°±0.20°, 19.9°±0.20°, and 23.0°±0.20° in an X-ray powder diffraction (XRPD) pattern.

Preferably, the aforesaid XRPD pattern of the ribociclib succinate in crystalline form B is substantially the same as shown in FIG. 1.

Another objective of the present invention is a ribociclib succinate in crystalline form C for preparing the aforesaid ribociclib succinate in crystalline form B, characterized by having characteristic peaks at 2θ values of 10.0°±0.20°, 20.0°±0.20°, 21.4°±0.20°, 23.0°±0.20°, and 27.9°±0.20° in an X-ray powder diffraction (XRPD) pattern.

Preferably, the aforesaid XRPD pattern of the ribociclib succinate in crystalline form C is substantially the same as shown in FIG. 4.

Another objective of the present invention is a ribociclib succinate in crystalline form D for preparing the aforesaid ribociclib succinate in crystalline form B, characterized by having characteristic peaks at 2θ values of 13.2°±0.20°, 18.1°±0.20°, 20.1°±0.20°, and 21.7°±0.20° in an X-ray powder diffraction (XRPD) pattern.

Preferably, the aforesaid XRPD pattern of the ribociclib succinate in crystalline form D is substantially the same as shown in FIG. 7.

Another objective of the present invention is ribociclib semi-succinate salt, which is a derivative of the aforesaid ribociclib succinate in crystalline form B, characterized by having characteristic peaks at 2θ values of 13.0°±0.20°, 16.2°±0.20°, 18.5°±0.20°, 20.1°±0.20°, and 22.1°±0.20° in an X-ray powder diffraction (XRPD) pattern.

Preferably, the aforesaid XRPD pattern of the ribociclib semi-succinate salt is substantially the same as shown in FIG. 10.

Another objective of the present invention is to provide a method for preparing the aforesaid ribociclib succinate in crystalline form B, C, or D, wherein the method includes the steps of slowly adding a solution containing 7-cyclopentyl-N,N-dimethyl-2-{[5-(piperazin-1-yl)pyridin-2-yl]amino}-7H-pyrrolo[2,3-d]pyrimidine-6-carboxamide into a succinic acid solution for reaction, stirring the mixed solution under high temperature, cooling the mixed solution, and then filtering the mixed solution to obtain a ribociclib succinate in crystalline form B, C, or D.

Preferably, the 7-cyclopentyl-N,N-dimethyl-2-{[5-(piperazin-1-yl)pyridin-2-yl]amino}-7H-pyrrolo[2,3-d]pyrimidine-6-carboxamide is obtained from the reaction of 7-cyclopentyl-N,N-dimethyl-7H-pyrrolo[2,3-d]pyrimidine-6-carbamide with 4-(6-aminopyrrol-3-yl)piperazin-1-carboxyl tert-butylate in the presence of lithium bis(trimethylsilyl) amine.

Preferably, the 7-cyclopentyl-N,N-dimethyl-2-{[5-(piperazin-1-yl)pyridin-2-yl]amino}-7H-pyrrolo[2,3-d]pyrimidine-6-carboxamide solution is at a temperature of 70-80° C., and the succinic acid solution is at a temperature of 30-80° C.

Another objective of the present invention is a pharmaceutical composition, comprising at least one component that is selected from a group consisting of the aforesaid ribociclib succinate in crystalline forms B, C, and D, ribociclib semi-succinate salt, and a composition that comprises at least two compounds selected from the group consisting of the aforesaid ribociclib succinate in crystalline forms B, C and D and ribociclib semi-succinate salt; and, a pharmaceutically acceptable vehicles, diluents, and excipients.

According to the above, the present invention uses lithium bis(trimethylsilyl)amine rather than the costly palladium acetate (Pd(OAc)$_2$) in preparing ribociclib succinates in crystalline forms B, C, and D so that production costs can be lowered. In addition, to reduce the residue of toxic organic solvents, a low-toxicity and highly volatile solvent such as ethanol or isopropanol is used to prepare ribociclib succinates in crystalline forms B and C. Moreover, the ribociclib succinate in crystalline form B prepared according to the present invention is stable in storage and insusceptible to degradation of its crystalline form as may otherwise result from changes in temperature or humidity. Thus, the present invention provides ribociclib succinates in crystalline forms B, C, and D and ribociclib semi-succinate salts suitable for industrial production and for use as therapeutic pharmaceutical compositions.

DETAILED DESCRIPTION OF THE INVENTION

The following Examples should not be regarded as unduly limiting the present invention. That the modification and exchanges of the following Examples done by a person having ordinary skilled is without departing from the spirit or the scope of the present invention may still fall within the scope of the present invention.

The terms "a", "an", "one" and "one kind" used herein mean the object phrase is one or more than one (at least one).

Figure 1:
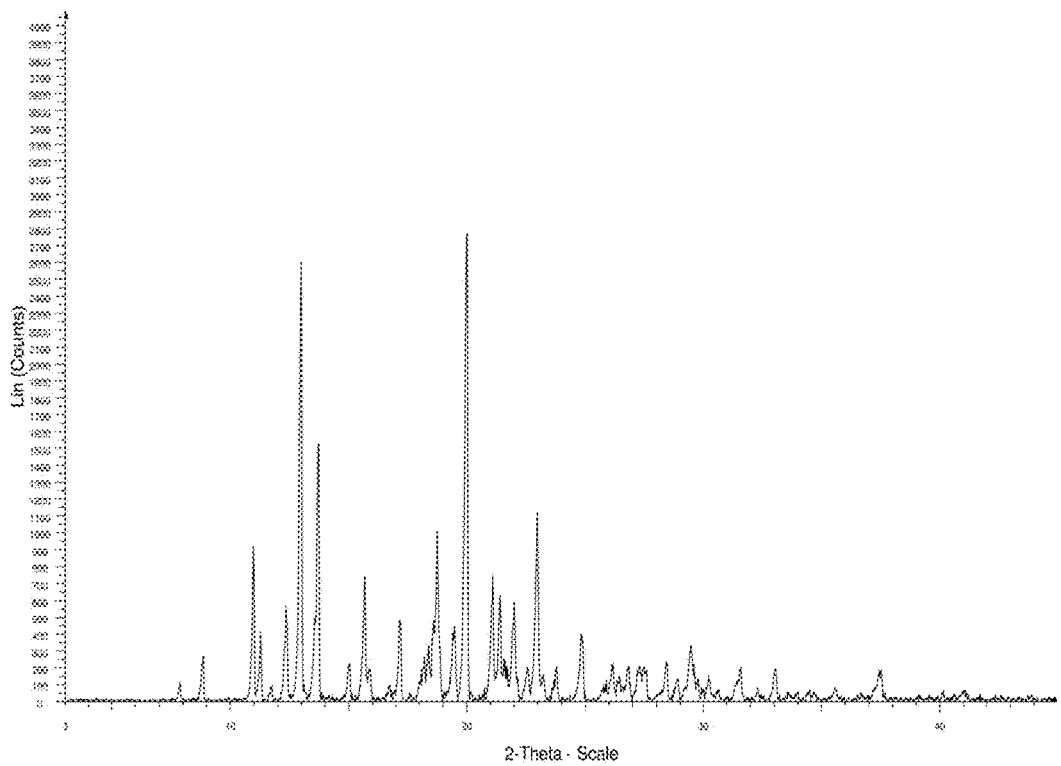
FIG. 1 is the XRPD pattern of the ribociclib succinate in crystalline form B of the present invention.

Ribociclib succinate in crystalline form B of the present application is characterized by having characteristic peaks at 2θ values of 12.9°±0.20, 13.7°±0.20°, 18.7°±0.20°, 19.9°±0.20°, and 23.0°±0.20° in an X-ray powder diffraction (XRPD) pattern, and further having secondary characteristic peaks (of lower intensities than the characteristic peaks) at 2θ values of 8.8°±0.20°, 15.4°±0.200, 17.2°±0.20°, and 24.8°±0.20° in the XRPD pattern. Typically, the XRPD pattern of the ribociclib succinate in crystalline form B is substantially the same as shown in FIG. 1.

Figure 4:
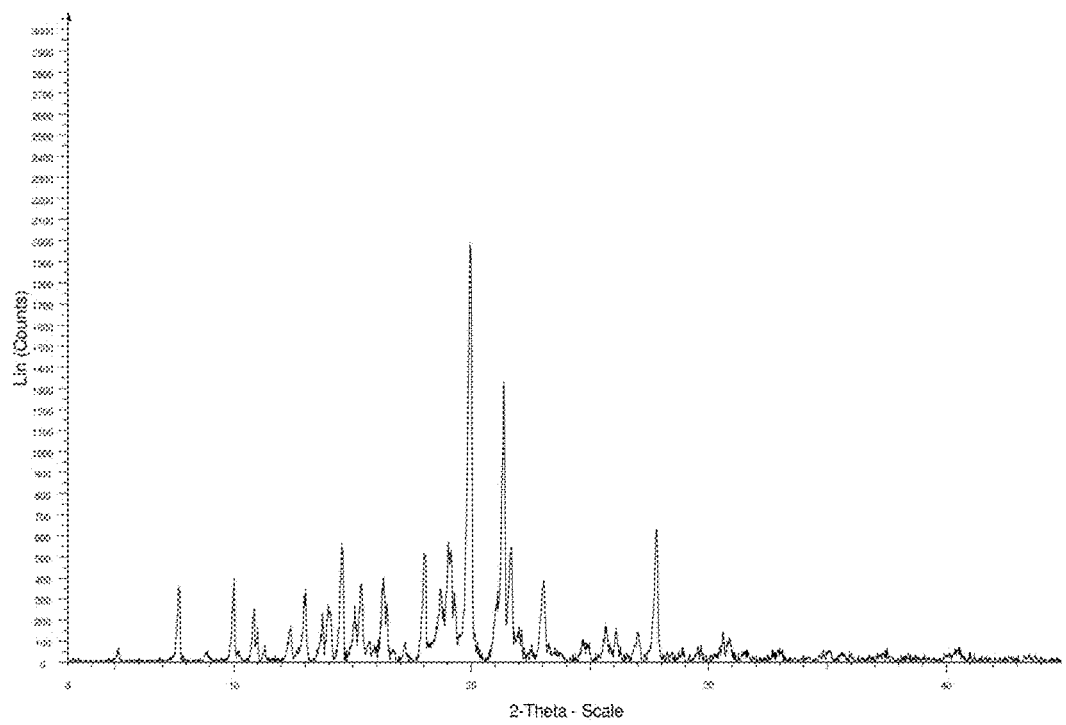
FIG. 4 is the XRPD pattern of the ribociclib succinate in crystalline form C of the present invention.

Ribociclib succinate in crystalline form C of the present invention for preparing the aforesaid ribociclib succinate in crystalline form B is characterized by having characteristic peaks at 2θ values of 10.0°±0.20°, 20.0°±0.20°, 21.4°±0.20°, 23.0°±0.20°, and 27.9°±0.20° in an XRPD pattern, and further having secondary characteristic peak (of lower intensity than the characteristic peaks) at the 20 value of 7.7°±0.20° in the XRPD pattern. Typically, the XRPD pattern of the ribociclib succinate in crystalline form C is substantially the same as shown in FIG. 4.

Figure 7:
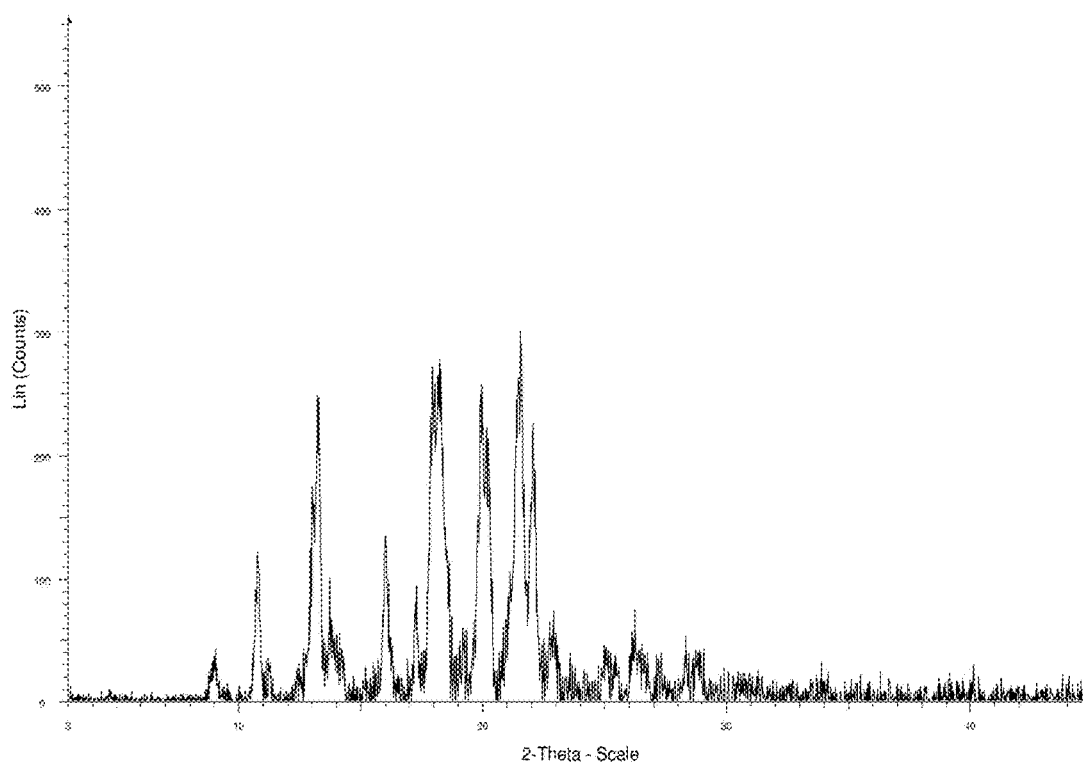
FIG. 7 is the XRPD pattern of the ribociclib succinate in crystalline form D of the present invention.

Ribociclib succinate in crystalline form D of the present invention for preparing the aforesaid ribociclib succinate in crystalline form B is characterized by having characteristic peaks at 2θ values of 13.2°±0.20°, 18.1°±0.20°, 20.1°±0.20°, and 21.7°±0.20° in an XRPD pattern, and further having secondary characteristic peaks (of lower intensities than the characteristic peaks) at 2θ values of 10.7°±0.20° and 16.0°±0.20° in the XRPD pattern. Typically, the XRPD pattern of the ribociclib succinate in crystalline form D is substantially the same as shown in FIG. 7.

Figure 10:
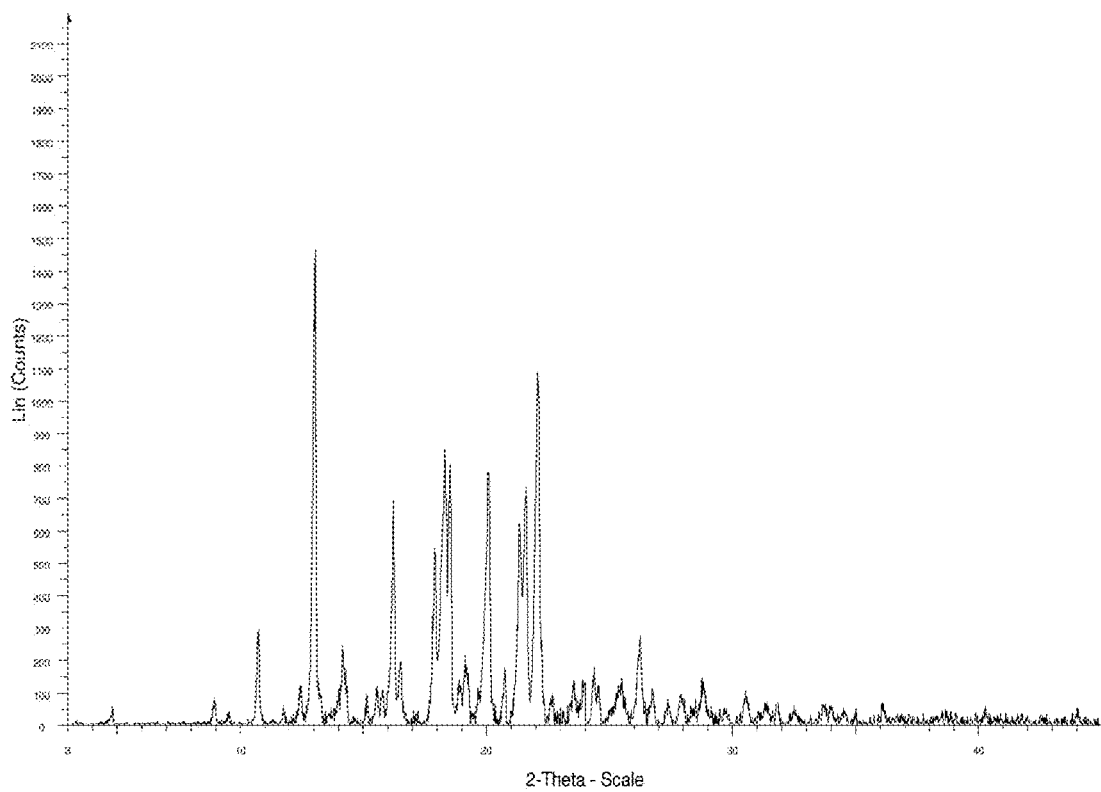
FIG. 10 is the XRPD pattern of the ribociclib semi-succinate of the present invention.

Rribociclib semi-succinate salt of the present invention is a derivative of the aforesaid ribociclib succinate in crystalline form B, characterized by having characteristic peaks at 2θ values of 13.0°±0.20°, 16.2°±0.20°, 18.5°±0.20, 20.1°±0.20°, and 22.1°±0.20° in an XRPD pattern, and further having secondary characteristic peaks (of lower intensities than the characteristic peaks) at 2θ values of 10.7°±0.20°, 14.2°±0.20°, 17.8°±0.20°, and 26.2°±0.20° in the XRPD pattern. Typically, the XRPD pattern of the ribociclib semi-succinate salt is substantially the same as shown in FIG. 10.

The methods of the present invention for preparing ribociclib succinates in crystal forms of B, C, and D and semi-succinates in various crystalline forms are described below.

I. Preparation method of 7-cyclopentyl-N,N-dimethyl-2-{[5-(piperazin-1-yl)pyridin-2-yl]amino}-7H-pyrrolo[2,3-d]pyrimidine-6-carboxamide The following is the scheme for the preparation method of 7-cyclopentyl-N,N-dimethyl-2-{[5-(piperazin-1-yl)pyridin-2-yl]amino}-7H-pyrrolo[2,3-d]pyrimidine-6-carboxamide:

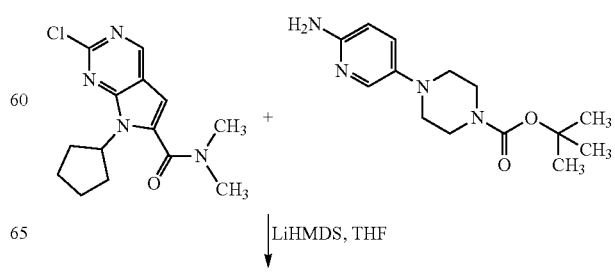

-continued

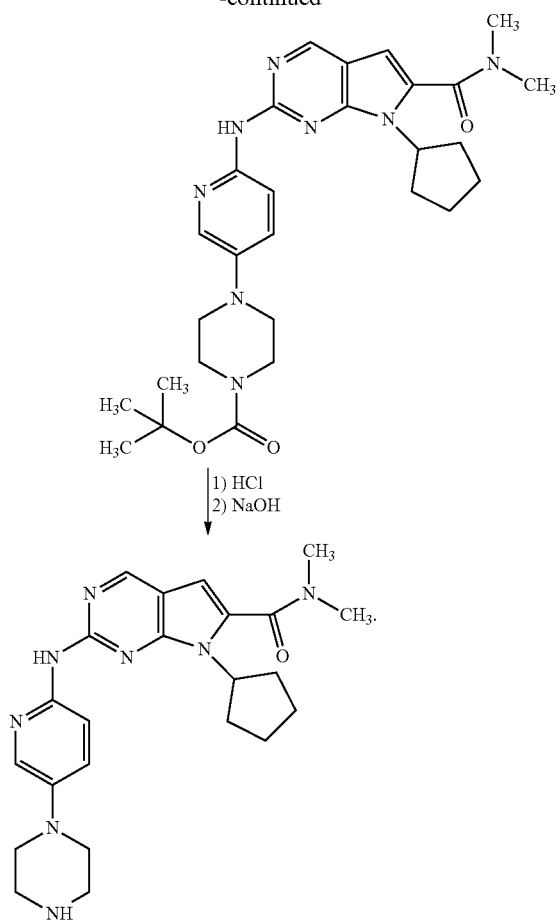

In a nitrogen environment at about 25±2° C., mix 2-chloro-7-cyclopentyl-N,N-dimethyl-7H-pyrrolo[2,3-d]pyrimidine-6-carbamide and 4-(6-aminopyyrol-3-yl)piperazin-1-carboxyl tert-butylate into tetrahydrofuran THF) added with lithium bis(trimethyl)amine (LiHMDS) and stir for about 1 h to obtain the intermediate 4-[6-[[7-cyclopentyl-6-[(dimethylamino)carbonyl]-7H-pyrrolo[2,3-pyrimidine-2-yl]amino]-3-pyridine]-1-piperazinecarboxyl 1,1-dimethylethylate. Cool the mixture to about 8±2° C. and keep the mixture at this temperature while an aqueous hydrogen chloride solution is subsequently added slowly and mixed into the mixture. After that, using a separatory funnel and ethyl acetate as an extracting agent, perform an extraction process in duplicate to acquire the aqueous phase. When the extracted solution is cooled to about 5° C. or lower, slowly add an aqueous sodium hydroxide solution until the pH reaches 12.5. Heat the solution to 25° C. and stir for about 16 h. Next, filter the solution to obtain the solid matter (or filter cake), and rinse the filter cake with DD water until the pH of the rinsing liquid is equal to or lower than 9. Lastly, dry the filter cake at about 55±5° C. to yield yellowish brown solids, which are 7-cyclopentyl-N,N-dimethyl-2-{[5-(piperazin-1-yl)pyridin-2-yl]amino}-7H-pyrrolo[2,3-d]pyrimidine-6-carboxamide, whose molar recovery rate can be 98% or higher, with 98% or higher purity.

More specifically, the 2-chloro-7-cyclopentyl-N,N-dimethyl-7H-pyrrolo[2,3-d]pyrimidine-6-carbamide, the 4-(6-aminopyridin-3-yl)piperazin-1-carboxyl tert-butylate, and the lithium bis(trimethylsilyl)amine (LiHMDS) are in an equivalent ratio of about 1:1:2.0 to 1:1:3.0, preferably 1:1:2.5, during the reaction.

II. Preparation Method (I) of Ribociclib Succinate in Crystalline Form B

The following is the scheme for the preparation method of ribociclib succinate in crystalline form B (I) of the present invention:

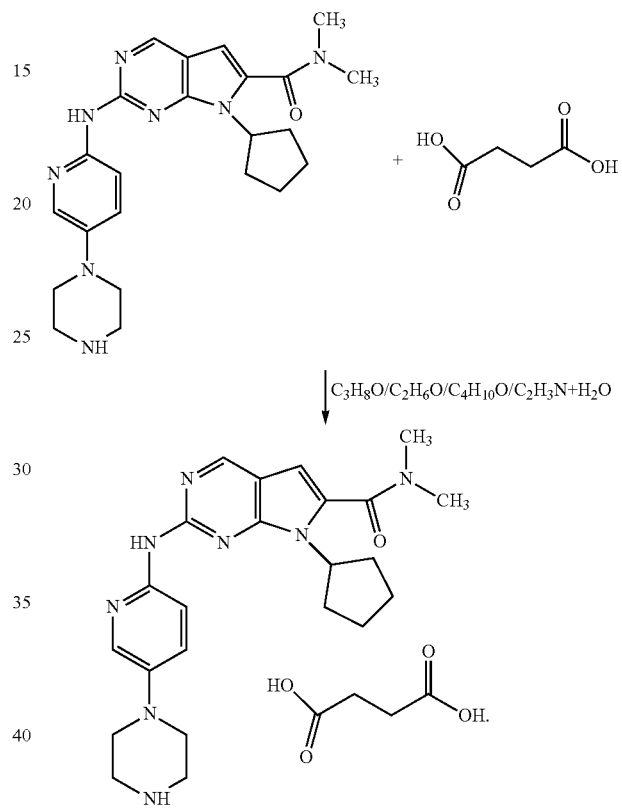

Add the 7-cyclopentyl-N,N-dimethyl-2-{[5-(piperazin-1-yl)pyridin-2-yl]amino}-7H-pyrrolo[2,3-d]pyrimidine-6-carboxamide prepared by the aforesaid preparation method into an organic solvent. Heat the solution to 80±5° C. and stir until complete dissolution was observed, producing a clear yellow solution. Cool the solution to 70±5° C., and then slowly add a succinic acid-containing organic solvent into the solution, whose temperature is kept at 75±2° C. The addition of the succinic acid-containing organic solvent takes about 10 to 35 min. After that, heat the solution to 70±10° C. and stir for about 2 h, with or without crystal seeds. Then cool the solution to 15±7° C. and stir for about 1 h. Following that, subject the solution to suction filtration to obtain a filter cake, which is subsequently rinsed with an alcohol-based organic solvent and then dried at about 55±5° C. to produce off-white solids, which are ribociclib succinate in crystalline form B. The molar recovery rate can be 95% or higher, and purity 98% or higher.

In the preparation method of ribociclib succinate in crystalline form B (I), the 7-cyclopentyl-N,N-dimethyl-2-{[5-(piperazin-1-yl)pyridin-2-yl]amino}-7H-pyrrolo[2,3-d]pyrimidine-6-carboxamide and the succinic acid are in an equivalent ratio of 1:1 to 1:1.1, preferably 1:1.05, during reaction. The organic solvent includes alcohol-based solvents and nitrile-based solvents. Applicable alcohol-based solvents include ethanol, isopropanol, 1-propanol, n-butanol, isobutanol, and so on. Applicable nitrile-based solvents include aqueous acetonitrile solutions. The crystal seeds include ribociclib succinate in crystalline form B and are added at 1% of the 7-cyclopentyl-N,N-dimethyl-2-{[5-(piperazin-1-yl)pyridin-2-yl]amino}-7H-pyrrolo[2,3-d]pyrimidine-6-carboxamide used (seeding 1%).

III. Preparation Method of Ribociclib Succinate in Crystalline Form C

The following is the scheme for the preparation method of ribociclib succinate in crystalline form C of the present invention:

In the preparation method of ribociclib succinate in crystalline form C, the 7-cyclopentyl-N,N-dimethyl-2-{[5-(piperazin-1-yl)pyridin-2-yl]amino}-7H-pyrrolo[2,3-d]pyrimidine-6-carboxamide and the succinic acid are in an equivalent ratio of 1:1 to 1:1.1, preferably 1:1.05, during reaction. The organic solvent includes isopropanol and isobutanol. The crystal seeds include ribociclib succinate in crystalline forms A and B, and are added at 1% of the 7-cyclopentyl-N,N-dimethyl-2-{[5-(piperazin-1-yl)pyridin-2-yl]amino}-7H-pyrrolo[2,3-d]pyrimidine-6-carboxamide used (seeding 1%).

IV. Preparation Method of Ribociclib Succinate in Crystalline Form D

The following is the scheme for the preparation method of ribociclib succinate in crystalline form D of the present invention:

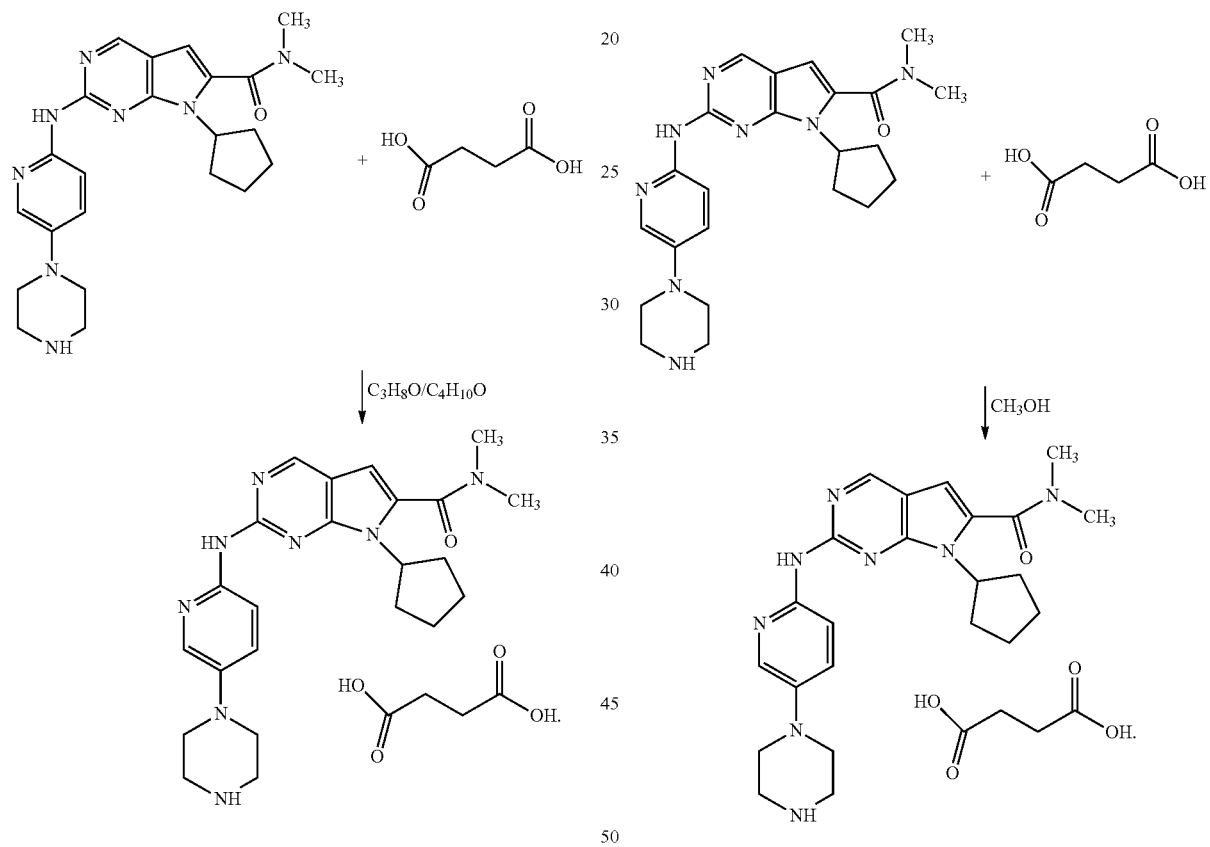

Add the 7-cyclopentyl-N,N-dimethyl-2-{[5-(piperazin-1-yl)pyridin-2-yl]amino}-7H-pyrrolo[2,3-d]pyrimidine-6-carboxamide prepared by the aforesaid preparation method into an organic solvent. Heat the solution to 80±5° C. and stir until complete dissolution was observed, producing a clear yellow solution. Cool the solution to 70±5° C., and then add a succinic acid-containing organic solvent into the solution in 3 to 4 min, whose temperature is kept at 70±2° C. After that, heat the solution to 80±2° C. and stir for about 1 h, with or without crystal seeds. Then cool the solution to 20±2° C. and stir for about 1 h. Following that, subject the solution to suction filtration to obtain a filter cake, which is subsequently rinsed with an alcohol-based organic solvent and then dried at about 55±5° C. to produce yellow solids, which are ribociclib succinate in crystalline form C. The molar recovery rate can be 93% or higher, and purity 98% or higher.

Add the 7-cyclopentyl-N,N-dimethyl-2-{[5-(piperazin-1-yl)pyridin-2-yl]amino}-7H-pyrrolo[2,3-d]pyrimidine-6-carboxamide prepared by the aforesaid preparation method into methanol. Heat the solution to 65±5° C. and stir until complete dissolution was observed, producing a clear yellow solution. Cool the solution to 60±2° C., and then add a succinic acid-containing methanol solution into the solution in about 5 min, whose temperature is kept at 60±2° C. After that, cool the solution to 55±2° C. and stir for about 1 h, with or without crystal seeds. Then cool the solution to 10±2° C. and stir for about 1 h. Following that, subject the solution to suction filtration to obtain a filter cake, which is subsequently rinsed with an alcohol-based organic solvent and then dried at about 55±5° C. to produce yellow solids, which are ribociclib succinate in crystalline form D. The molar recovery rate can be 90% or higher, and purity 98% or higher.

In the preparation method of ribociclib succinate in crystalline form D, the 7-cyclopentyl-N,N-dimethyl-2-{[5-(piperazin-1-yl)pyridin-2-yl]amino}-7H-pyrrolo[2,3-d]pyrimidine-6-carboxamide and the succinic acid are in an equivalent ratio of 1:1 to 1:1.1, preferably 1:1.05, during reaction. The crystal seeds include ribociclib succinate in crystalline form B, and are added at 1% of the 7-cyclopentyl-N,N-dimethyl-2-{[5-(piperazin-1-yl)pyridin-2-yl]amino}-7H-pyrrolo[2,3-d]pyrimidine-6-carboxamide used (seeding 1%).

V. Preparation Method (II) of Ribociclib Succinate in Crystalline Form B

In addition to the aforesaid preparation method (I) of ribociclib succinate in crystalline form B, ribociclib succinate in crystalline form B according to the present invention can also be obtained by polymorph transformation of ribociclib succinates in other crystalline forms, as described below:

Dissolve the aforesaid ribociclib succinate in crystalline form C or brand-name ribociclib succinate in crystalline form A in isopropanol and heat to 80±2° C. Stir for about 1 h. Add the aforesaid ribociclib succinate in crystalline form B as crystal seeds and stir the solution for about 2 h while the temperature is kept at 80±2° C. Then cool the solution to 20±2° C. and stir for about 1 h. Filter the solution to obtain a filter cake. Rinse the filter cake with the aforesaid alcohol-based solvent and then dry at about 55±5° C. to produce off-white solids, which are ribociclib succinate in crystalline form B. The recovery rate can be 93% or higher.

In the preparation method (II) of ribociclib succinate in crystalline form B, the addition of ribociclib succinate in crystalline form B as crystal seeds is optional. When added as crystal seeds, ribociclib succinate in crystalline form B is added at about 1% of the total mass of the ribociclib succinate in crystalline forms A or C.

VI. Preparation Method of Crystalline Ribociclib Semi-Succinate

The following is the scheme for the preparation method of crystalline ribociclib semi-succinate of the present invention:

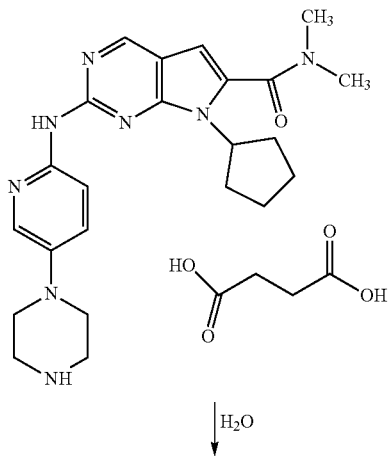

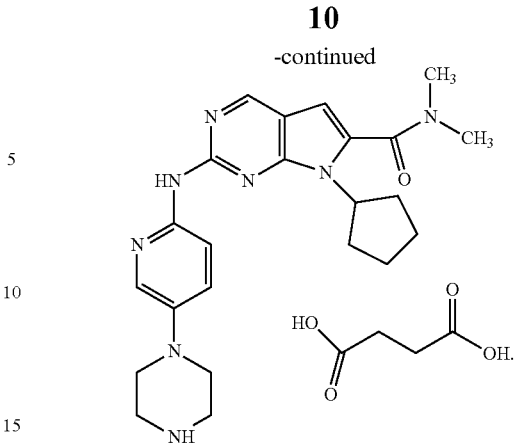

Dissolve the aforesaid ribociclib succinate in crystalline form B in water or an aqueous isopropanol solution with more than 6.4% of water. Stir the mixture at 25 to 80° C. for about 1 to 2 h and then at 20±2° C. for about 1 h. Filter the solution to obtain a filter cake. Rinse the filter cake with a small volume of water and then dry at about 55±5° C. to produce yellow solids, which are crystalline ribociclib semi-succinate.

In the present invention, the determinants of obtaining ribociclib succinate in crystalline form B, C, or D from the reaction of 7-cyclopentyl-N,N-dimethyl-2-{[5-(piperazin-1-yl)pyridin-2-yl]amino}-7H-pyrrolo[2,3-d]pyrimidine-6-carboxamide and succinic acid are: (1) the type of the organic solvent used for the reaction of 7-cyclopentyl-N,N-dimethyl-2-{[5-(piperazin-1-yl)pyridin-2-yl]amino}-7H-pyrrolo[2,3-d]pyrimidine-6-carboxamide with succinic acid, and (2) the duration of succinic acid addition. First of all, the organic solvent used in the preparation of ribociclib succinate in crystalline form B can be ethanol, isopropanol, 1-propanol, n-butanol, isobutanol, or acetonitrile aqueous solution; the organic solvent used in the preparation of ribociclib succinate in crystalline form C can be isopropanol or isobutanol; and the organic solvent used in the preparation of ribociclib succinate in crystalline form D is methanol. While isopropanol or isobutanol can be used as the organic solvent in the preparation of ribociclib succinate in crystalline form B or C, crystalline form C is formed only with the fast addition of succinic acid. In other words, when isopropanol or isobutanol is used as the organic solvent for dissolving 7-cyclopentyl-N,N-dimethyl-2-{[5-(piperazin-1-yl)pyridin-2-yl]amino}-7H-pyrrolo[2,3-d]pyrimidine-6-carboxamide, ribociclib succinate in crystalline form B will be produced if succinic acid has been added by slow addition. Secondly, the most important factor in the synthesis of ribociclib succinate in crystalline form D is to use methanol as the organic solvent for dissolving 7-cyclopentyl-N,N-dimethyl-2-{[5-(piperazin-1-yl)pyridin-2-yl]amino}-7H-pyrrolo[2,3-d]pyrimidine-6-carboxamide. 7-cyclopentyl-N,N-dimethyl-2-{[5-(piperazin-1-yl)pyridin-2-yl]amino}-7H-pyrrolo[2,3-d]pyrimidine-6-carboxamide dissolved in methanol will react with succinic acid to produce ribociclib succinate in crystalline form D regardless of the duration of succinic acid addition and the use or lack of use of crystal seeds.

According to the present invention, ribociclib semi-succinates can be produced by reacting ribociclib succinate in crystalline form B with water or an isopropanol solution with more than 6.4% of water.

The pharmaceutical composition of the present invention comprises at least one component that is selected from a group consisting of the aforesaid ribociclib succinate in crystalline forms B, C and D, ribociclib semi-succinate salt, and a composition that comprises at least two compounds selected from the group consisting of the ribociclib succinate B, C and D and ribociclib semi-succinate salt; and, pharmaceutically acceptable vehicles, diluents, and excipients.

The present invention also provides pharmaceutical compositions that can inhibit cyclin-dependent kinases (CDKs), e.g., CDK1, CDK2, CDK3, CDK4, CDK5, CDK6, and CDK9, particularly CDK4 and CDK6. These pharmaceutical compositions can be used to treat diseases requiring CDK inhibition such as breast cancer, lung cancer, urinary and reproductive cancer, gastrointestinal cancer, melanoma, ovarian cancer, pancreatic cancer, neuroblastoma, bone cancer, prostate cancer, small-cell lung carcinoma, glioblastoma, colorectal cancer, kidney cancer, epithelial cancer, liver cancer, esophageal cancer, leukemia, lymphoma, bone marrow cancer, fibrosarcoma, epithelioid sarcoma, and follicular thyroid carcinoma, particularly breast cancer, and more particularly advanced or recurrent breast cancer.

The vehicles, diluents, and excipients used in the present invention are those generally used in the art; the invention has no limitation in this regard.

The pharmaceutical compositions of the present invention can be prepared into any general dosage forms, including tablet, powder, capsule, suppository, suspension, liposome, and spray.

EXAMPLES

In the following Examples 1 to 21, comparative example, and testing example, an X-ray diffractometer (Bruker D8 ADVANCE X-Ray Diffractometer) was used with the operation and analysis parameters below:
X-ray reflection parameter: Cu-Kα
Kα1(Å): 1.540562 Å
Voltage: 40 kV
Current: 40 mA
Start of scan (2θ): 3.000°
End of scan (2θ): 45.000°
Step size (2θ): 0.020°
Number of steps: 2140
Step duration: 2 seconds/step
Sample revolving speed: 15 rpm
In Examples 2, 12, 14, and 16, a differential scanning calorimeter (DSC) (Perkin Elmer DSC-7 Calorimeter) was used with the operation and analysis parameters below:
Scanning rate: 10° C. per minute
Temperature range: 40° C. to 240° C.
Protecting gas: 99.99% nitrogen gas Example 1. Preparation of 7-cyclopentyl-N,N-dimethyl-2-{[5-(piperazin-1-yl)pyridin-2-yl]amino}-7H-pyrrolo[2,3-d]pyrimidine-6-carboxamide 10.0 g of 2-chloro-7-cyclopentyl-N,N-dimethyl-7H-pyrrolo[2,3-d]pyrimidine-6-carbamide, 4-(6-aminopyridin-3-yl)piperazin-1-carboxyl tert-butylate (1.00 eq) and 9.59 g of 4-(6-aminopyridin-3-yl)piperazin-1-carboxyl tert-butylate (1.01 eq) were added into a 1-liter three-neck flask. Then, in a nitrogen environment, 230 mL tetrahydrofuran was added, and the solution was stirred for 10 min until complete dissolution was observed. After that, 86 mL 1.0M lithium bis(trimethylsilyl)amine in tetrahydrofuran (2.52 eq) was added slowly at 18±3° C., and the solution was stirred at 25±2° C. for 1 h, until the relative area percentage of the reactant 2-chloro-7-cyclopentyl-N,N-dimethyl-7H-pyrrolo[2,3-d]pyrimidine-6-carbamide was equal to or lower than 1.0% as indicated by a high-performance liquid chromatography (HPLC) system. The solution was cooled to 8±2° C. and then slowly added with 171 mL 2N aqueous hydrogen chloride solution (10 eq) while the temperature remained at 8±2° C. The solution was then heated to 48±2° C. and stirred for 2 h, until the relative area percentage of the intermediate 4[6-[[7-cyclopentyl-6-[(dimethylamino)carbonyl]-7H-pyrrolo[2,3-d]pyrimidin-2-yl]amino]3-pyridine]-1-piperazinecarboxyl 1,1-dimethylethylate was equal to or lower than 1.0% as indicated by the HPLC system. Following that, the solution was cooled to 35±2° C. and then transferred into a 1-liter separatory funnel, into which 200 mL ethyl acetate was subsequently added for extraction. The solution was left until stratified, and the aqueous phase was obtained. The same ethyl acetate extraction process was repeated twice to yield more aqueous phase. The collected aqueous phase was transferred into a 500-mL round-bottom flask and cooled to 5±2° C. in a water bath. Then, 100 mL 10% aqueous sodium hydroxide solution was added slowly until the pH of the solution reached 13±0.5. The solution was then allowed to cool down slowly to ambient temperature (25±3° C.) and was stirred for 16 h. Solids were obtained through suction filtration and were rinsed multiple times with 125 mL DD water until the pH of the rinsing liquid was equal to or lower than 9. The filter cake was dried in a vacuum oven at 55±5° C. for 17 h, producing approximately 14.529 g of 7-cyclopentyl-N,N-dimethyl-2-{[5-(piperazin-1-yl)pyridin-2-yl]amino}-7H-pyrrolo[2,3-d]pyrimidine-6-carboxamide in the form of yellowish brown solids, with 98% purity, the molar recovery rate being 98%.

Example 2. Preparation of Ribociclib Succinate in Crystalline Form B (by the Preparation Method (I) of Ribociclib Succinate in Crystalline Form B of the Present Invention Using Isopropanol as the Organic Solvent, without Crystal Seeds)

Figure 2:
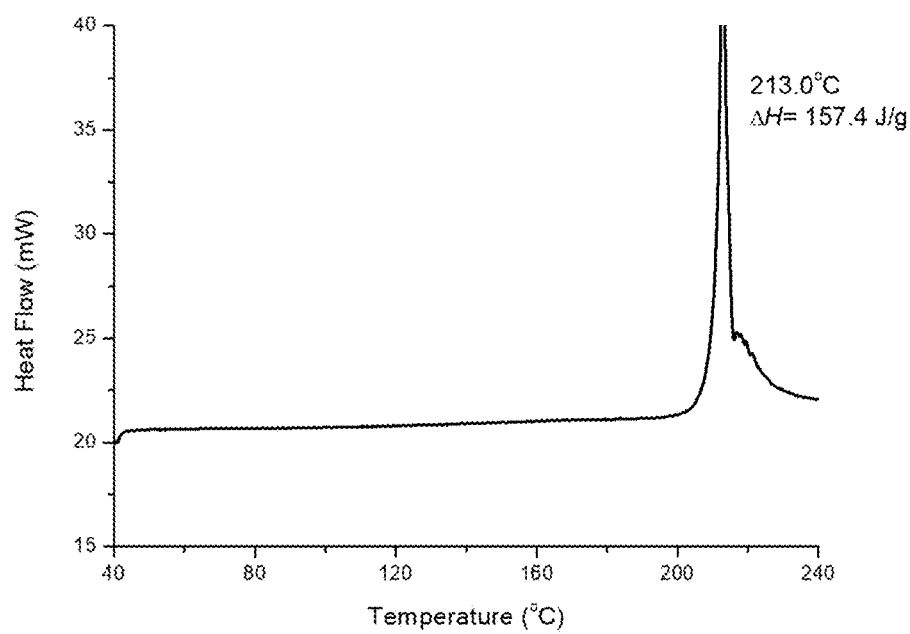
FIG. 2 is the DSC curve of the ribociclib succinate in crystalline form B of the present invention.
Figure 3:
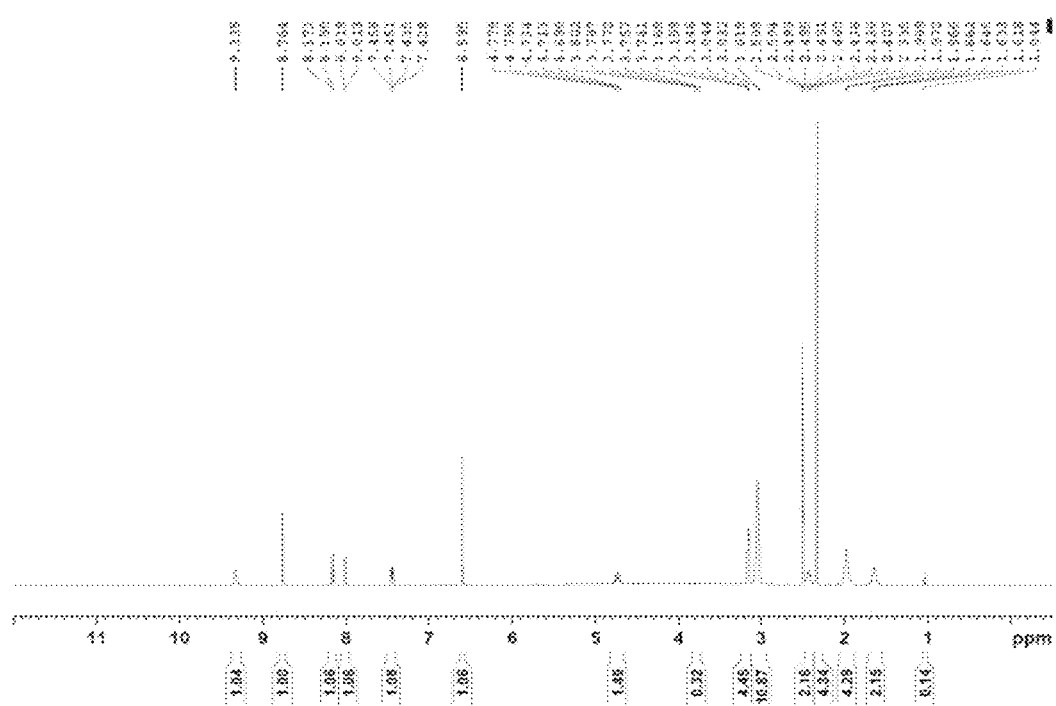
FIG. 3 is the nuclear magnetic hydrogen spectrum of the ribociclib succinate in crystalline form B of the present invention.

A nitrogen-flushed 250-mL round bottom flask was charged with 3.33 g (1.05 eq) of succinic acid and 93 mL isopropanol (iPrOH). The resulted solution was heated to 60±2° C., and stirred until the solids were fully dissolved, producing a clear solution. The heated succinic acid/iPrOH solution was then filtered through filter paper, and the filtrate was maintained at 40-2° C. A nitrogen-flushed four-neck round bottom flask was charged with 11.66 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide, and 424 mL isopropanol. The resulted solution was heated to 80±2° C., and stirred for 1 h, until complete dissolution was observed, producing a clear yellow solution. The yellow solution was cooled to 75±2° C., added with the prepared 40±2° C. of succinic acid/iPrOH solution over 35 min, and then maintained at 75±2° C. After that, the mixed solution was heated to 80±2° C. and stirred for 2 h. Then the mixed solution was cooled to 20±2° C. and stirred for 1 h A filter cake was subsequently obtained through suction filtration, rinsed with 10 mL isopropanol, and then dried in the vacuum oven at 55±5° C. for 16 h Approximately 14.1 g of ribociclib succinate in crystalline form B was obtained as off-white solids (approximately 95% molar recovery rate); the ribociclib succinate product had 99.8% purity, 0.5 wt % water, and 20.1 wt % succinic acid. FIG. 1, FIG. 2, and FIG. 3 show an X-ray powder diffraction (XRPD) pattern, a DSC curve, and a nuclear magnetic hydrogen spectrum of the product respectively.

Example 3. Preparation of Ribociclib Succinate in Crystalline Form B (by the Preparation Method (I) of Ribociclib Succinate in Crystalline Form B of the Present Invention Using Isopropanol as the Organic Solvent, with Crystal Seeds)

A nitrogen-flushed 20-mL round bottom flask was charged with 0.57 g (1.05 eq) of succinic acid and 16 mL isopropanol (iPrOH). The resulted solution was heated to 60±2° C., and stirred until the solids were fully dissolved, producing a clear solution. The heated succinic acid/iPrOH solution was then filtered through filter paper, and the filtrate was maintained at 40±2° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 73 mL isopropanol. The resulted solution was heated to 80±2° C. and stirred for 1 h, until complete dissolution was observed, producing a clear yellow solution. The yellow solution was cooled to 75±2° C., added with the prepared 40±2° C. of succinic acid/iPrOH solution over 10 min, and then maintained at 75±2° C. The solution was added 1% of ribociclib succinate in crystalline form B as crystal seed, and then a large amount of solid was precipitated after adding crystal seed. After that, the mixed solution was heated to 80±2° C. and stirred for 1 h. Then the mixed solution was cooled to 20±2° C. and stirred for 1 h. A filter cake was subsequently obtained through suction filtration, rinsed with 2 mL isopropanol, and then dried in the vacuum oven at 55±5° C. for 16 h. Approximately 2.4 g of ribociclib succinate in crystalline form B was obtained as off-white solids (approximately 94% molar recovery rate).

Example 4. Preparation of Ribociclib Succinate in Crystalline Form B (by the Preparation Method (I) of Ribociclib Succinate in Crystalline Form B of the Present Invention Using Ethanol as the Organic Solvent, with Crystal Seeds)

A nitrogen-flushed 1-L four-neck flask was charged with 45.0 g (1.05 eq) of succinic acid and 900 mL ethanol (EtOH). The resulted solution was heated to 60±2° C., and stirred until the solids were fully dissolved, producing a clear solution. The heated succinic acid/EtOH solution was then filtered through filter paper, and the filtrate was maintained at 50±5° C. A nitrogen-flushed 5-L four-neck flask was charged with 158.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 3300 mL ethanol. The resulted solution was heated to 78±2° C. and stirred for 1 h, until complete dissolution was observed, producing a clear yellow solution. The yellow solution was cooled to 7012° C., added with the prepared 50±5° C. of succinic acid/EtOH solution over 50 min, and then maintained at 7012° C. The solution was added 1% of ribociclib succinate in crystalline form B as crystal seed, and then an amount of solid was gradually precipitated. After that, the mixed solution was cooled to 65±2° C. and stirred for 2 h. Then the mixed solution was cooled to 1012° C. and stirred for 1 h. A filter cake was subsequently obtained through suction filtration, rinsed with 150 mL and 5±2° C. of ethanol, and then dried in the vacuum oven at 55±5° C. for 16 h. Approximately 188.0 g of ribociclib succinate in crystalline form B was obtained as pale yellow solids (approximately 94% molar recovery rate).

Example 5. Preparation of Ribociclib Succinate in Crystalline Form B (by the Disclosed Preparation Method (I) of Ribociclib Succinate in Crystalline Form B, Using Ethanol as the Organic Solvent, without Crystal Seeds)

A nitrogen-flushed 20-mL round bottom flask was charged with 0.57 g (1.05 eq) of succinic acid and 11 mL ethanol (EtOH). The resulted solution was heated to 76±2° C., and stirred until the solids were fully dissolved, producing a clear solution. The heated succinic acid/EtOH solution was then filtered through filter paper, and the filtrate was maintained at 50±5° C. A nitrogen-flushed 5-L four-neck flask was charged with 2.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 42 mL ethanol. The resulted solution was heated to 76±2° C. and stirred for 1 h, until complete dissolution was observed, producing a clear yellow solution. The yellow solution was cooled to 70±2° C., added with the prepared 50±5° C. of succinic acid/EtOH solution over 20 min, and then maintained at 70±2° C. After that, the mixed solution was cooled to 58±2° C. and stirred for 2 h. Then the mixed solution was cooled to 10±2° C. and stirred for 1 h. A filter cake was subsequently obtained through suction filtration, rinsed with 6 mL and 5±2° C. of ethanol, and then dried in the vacuum oven at 55±5° C. for 16 h. Approximately 2.22 g of ribociclib succinate in crystalline form B was obtained as pale yellow solids (approximately 87% molar recovery rate).

Example 6. Preparation of Ribociclib Succinate in Crystalline Form B (by the Preparation Method (I) of Ribociclib Succinate in Crystalline Form B of the Present Invention Using n-Butanol as the Organic Solvent, with Crystal Seeds)

A nitrogen-flushed 20-mL round bottom flask was charged with 0.57 g (1.05 eq) of succinic acid and 16 mL n-butanol (nBuOH). The resulted solution was heated to 90±2° C., and stirred until the solids were fully dissolved, producing a clear solution. The heated succinic acid/nBuOH solution was then filtered through filter paper, and the filtrate was maintained at 75±5° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 73 mL n-butanol. The resulted solution was heated to 82±2° C. and stirred for 1 h, until complete dissolution was observed, producing a clear yellow solution. The yellow solution was cooled to 75±2° C., added with the prepared succinic acid/nBuOH solution over 25 min, and then maintained at 75±2° C. The solution was added 1% of ribociclib succinate in crystalline form B as crystal seed, and then a large amount of solid was precipitated. After that, the mixed solution was cooled to 70±2° C. and stirred for 1 h, and cooled to 20±2° C. and stirred for 1 h. A filter cake was subsequently obtained through suction filtration, rinsed with 5±2° C. of n-butanol, and then dried in the vacuum oven at 55±5° C. for 16 h. Approximately 2.37 g of ribociclib succinate in crystalline form B was obtained as pale yellow solids (approximately 93% molar recovery rate).

Example 7. Preparation of Ribociclib Succinate in Crystalline Form B (by the Disclosed Preparation Method (I) of Ribociclib Succinate in Crystalline Form B, Using n-Butanol as the Organic Solvent, without Crystal Seeds)

A nitrogen-flushed 20-mL round bottom flask was charged with 0.57 g (1.05 eq) of succinic acid and 16 mL n-butanol (nBuOH). The resulted solution was heated to 90±2° C., and stirred until the solids were fully dissolved, producing a clear solution. The heated succinic acid/nBuOH solution was then filtered through filter paper, and the filtrate was maintained at 75±5° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 73 mL n-butanol. The resulted solution was heated to 82±2° C. and stirred for 1 h, until complete dissolution was observed, producing a clear yellow solution. The yellow solution was cooled to 75±2° C., added with the prepared 75±2° C. of succinic acid/nBuOH solution over 25 min, and then maintained at 75±2° C. The mixed solution was cooled to 72° C. and precipitated with solids. After that, the mixed solution was cooled to 70±2° C. and stirred for 1 h. Then the mixed solution was cooled to 20±2° C. and stirred for 1 h. A filter cake was subsequently obtained through suction filtration, rinsed with 5±2° C. of n-butanol, and then dried in the vacuum oven at 55±5° C. for 16 h. Approximately 2.34 g of ribociclib succinate in crystalline form B was obtained as white-off solids (approximately 92% molar recovery rate).

Example 8. Preparation of Ribociclib Succinate in Crystalline Form B (by the Disclosed Preparation Method (I) of Ribociclib Succinate in Crystalline Form B, Using Isobutanol as the Organic Solvent, without Crystal Seeds)

A nitrogen-flushed 20-mL round bottom flask was charged with 0.57 g (1.05 eq) of succinic acid and 16 mL isobutanol (iBuOH). The resulted solution was heated to 60±2° C., and stirred until the solids were fully dissolved, producing a clear solution. The heated succinic acid/iBuOH solution was then filtered through filter paper, and the filtrate was maintained at 60±5° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 74 mL isobutanol. The resulted solution was heated to 80±2° C. and stirred for 1 h, until complete dissolution was observed, producing a clear yellow solution. The yellow solution was cooled to 75±2° C., added with the prepared 60±5° C. of succinic acid/iBuOH solution over 10 min, and then maintained at 75±2° C. After that, the mixed solution was heated to 78±2° C. and stirred for 1 h. Then the mixed solution was cooled to 20±2° C. and stirred for 1 h. A filter cake was subsequently obtained through suction filtration, rinsed with 5 mL and 5±2° C. of isobutanol, and then dried in the vacuum oven at 55±5° C. for 16 h. Approximately 2.4 g of ribociclib succinate in crystalline form B was obtained as pale yellow solids (approximately 94% molar recovery rate).

Example 9. Preparation of Ribociclib Succinate in Crystalline Form B (by the Disclosed Preparation Method (I) of Ribociclib Succinate in Crystalline Form B, Using Aqueous Acetonitrile Solutions as the Organic Solution, without Crystal Seeds)

A nitrogen-flushed 20-mL round bottom flask was charged with 0.283 g (1.05 eq) of succinic acid and an aqueous acetonitrile (ACN) solution containing 5.6 mL acetonitrile and 0.2 mL water. The resulted solution was heated to 65±2° C., and stirred until the solids were fully dissolved, producing a clear solution. The heated succinic acid/ACN solution was then filtered through filter paper, and the filtrate was maintained at 60±5° C. A nitrogen-flushed 250-mL three-neck flask was charged with 1.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide, 80 mL acetonitrile and 1.6 mL water. The resulted solution was heated to 76±2° C. and stirred for 1 h, until complete dissolution was observed, producing a clear yellow solution. The yellow solution was cooled to 78±2° C., added with the prepared 60±5° C. of succinic acid/ACN solution over 3 min, and then maintained at 78±2° C. After that, the mixed solution was heated to 78±2° C. and stirred for 45 min. Then the mixed solution was cooled to 18±2° C. and stirred for 1 h. A filter cake was subsequently obtained through suction filtration, rinsed with 5 mL and 5±2° C. of acetonitrile, and then dried in the vacuum oven at 55±5° C. for 16 h. Approximately 1.035 g of ribociclib succinate in crystalline form B was obtained as pale yellow solids (approximately 81.4% molar recovery rate).

Example 10. Preparation of Ribociclib Succinate in Crystalline Form B (by the Preparation Method (I) of Ribociclib Succinate in Crystalline Form B of the Present Invention Using 1-Propanol as the Organic Solvent, with Crystal Seeds)

A nitrogen-flushed 20-mL round bottom flask was charged with 0.57 g (1.05 eq) of succinic acid and 16 mL 1-propanol (nPrOH). The resulted solution was heated to 60±2° C., and stirred until the solids were fully dissolved, producing a clear solution. The heated succinic acid/nPrOH solution was then filtered through filter paper, and the filtrate was maintained at 60±5° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 74 mL 1-propanol. The resulted solution was heated to 80±2° C. and stirred for 1 h, until complete dissolution was observed, producing a clear yellow solution. The yellow solution was cooled to 75±2° C., added with the prepared succinic acid/nPrOH solution over 3 min, and then maintained at 75±2° C. The solution was added 1% of ribociclib succinate in crystalline form B as crystal seed, and then a large amount of solid was precipitated. The mixed solution was cooled to 78±2° C. and stirred for 1 h, and then cooled to 20±2° C. and stirred for 1 h. A filter cake was subsequently obtained through suction filtration, rinsed with 5±2° C. of 1-propanol, and then dried in the vacuum oven at 55±5° C. for 16 h. Approximately 2.4 g of ribociclib succinate in crystalline form B was obtained as pale yellow solids (approximately 94% molar recovery rate).

Example 11. Preparation of Ribociclib Succinate in Crystalline Form B (by the Disclosed Preparation Method (I) of Ribociclib Succinate in Crystalline Form B, Using 1-Propanol as the Organic Solvent, without Crystal Seeds)

A nitrogen-flushed 20-mL round bottom flask was charged with 0.57 g (1.05 eq) of succinic acid and 16 mL 1-propanol (nPrOH). The resulted solution was heated to 60±2° C., and stirred until the solids were fully dissolved, producing a clear solution. The heated succinic acid/nPrOH solution was then filtered through filter paper, and the filtrate was maintained at 60±5° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]

amino}-7H-pyrrolo[2,3-d]pyrimidine-6-carboxamide and 74 mL 1-propanol. The resulted solution was heated to 80±2° C. and stirred for 1 h, until complete dissolution was observed, producing a clear yellow solution. The yellow solution was cooled to 75±2° C., added with the prepared succinic acid/nPrOH solution over 3 min, and then maintained at 75±2° C. After that, the mixed solution was heated to 75±2° C. and stirred for 1 h. Then the mixed solution was cooled to 20±2° C. and stirred for 1 h. A filter cake was subsequently obtained through suction filtration, rinsed with 5±2° C. of 1-propanol, and then dried in the vacuum oven at 55±5° C. for 16 h. Approximately 2.35 g of ribociclib succinate in crystalline form B was obtained as white-off solids (approximately 92% molar recovery rate).

Example 12. Preparation of Ribociclib Succinate in Crystalline Form C (by the Disclosed Preparation Method of Ribociclib Succinate in Crystalline Form C, Using Isopropanol as the Organic Solvent, without Crystal Seeds)

Figure 5:
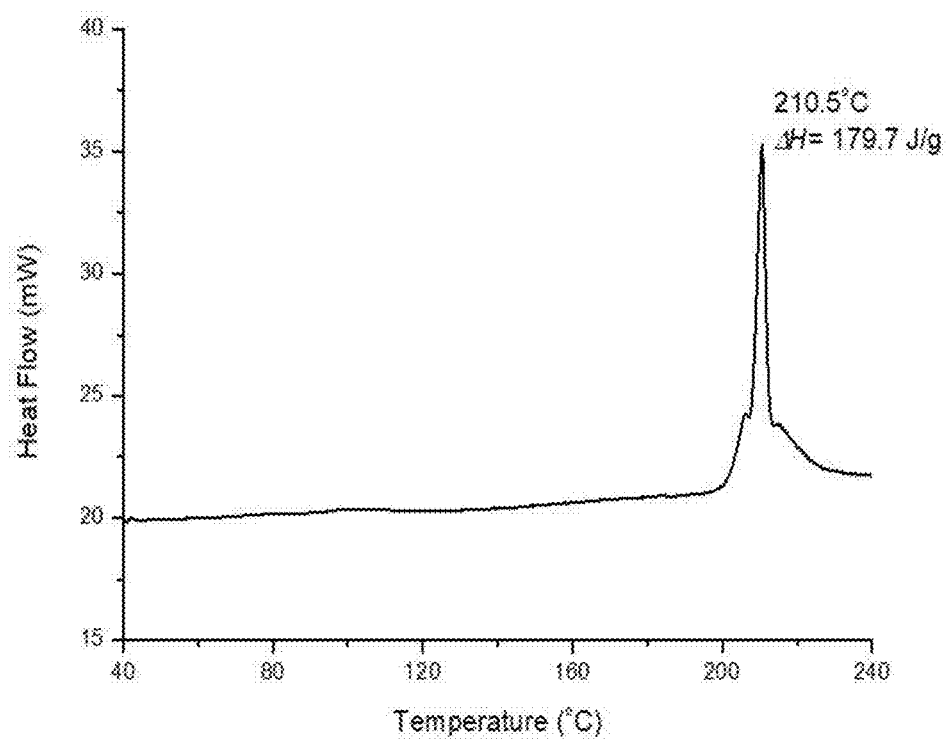
FIG. 5 is the DSC curve of the ribociclib succinate in crystalline form C of the present invention.
Figure 6:
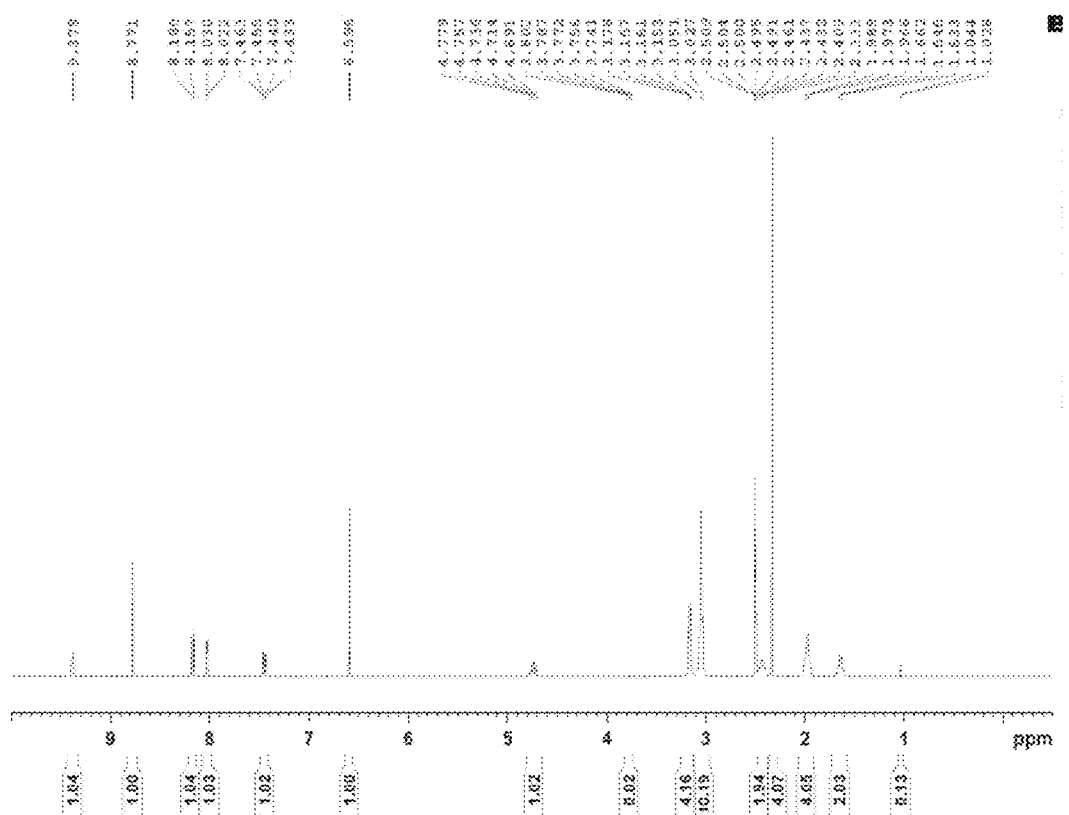
FIG. 6 is the nuclear magnetic hydrogen spectrum of the ribociclib succinate in crystalline form C of the present invention.

A nitrogen-flushed 20-mL round bottom flask was charged with 0.57 g (1.05 eq) of succinic acid and 16 mL isopropanol (iPrOH). The resulted solution was heated to 60±2° C., and stirred until the solids were fully dissolved, producing a clear solution. The heated succinic acid/iPrOH solution was then filtered through filter paper, and the filtrate was maintained at 40±2° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2, 3-d]pyrimidine-6-carboxamide and 73 mL isopropanol. The resulted solution was heated to 80±2° C. and stirred for 1 h, until complete dissolution was observed, producing a clear yellow solution. The yellow solution was cooled to 70±2° C., added with the prepared 40±2° C. of succinic acid/iPrOH solution over 4 min, and then maintained at 70±2° C.; meanwhile, an amount of solids started to form when about 60% of the succinic acid isopropanol solution had been added. After that, the mixed solution was heated to 80±2° C. and stirred for 1 h. Then the mixed solution was cooled to 20±2° C. and stirred for 1 h. A filter cake was subsequently obtained through suction filtration, rinsed with 2 mL isopropanol, and then dried in the vacuum oven at 55±5° C. for 16 h. Approximately 2.36 g of ribociclib succinate in crystalline form C was obtained as pale yellow solids (approximately 93% molar recovery rate). The ribociclib succinate product had 99.8% purity, 1.3 wt % water, and 20.9 wt % succinic acid. FIG. 4, FIG. 5, and FIG. 6 show an XRPD pattern, a DSC curve, and a nuclear magnetic hydrogen spectrum of the product respectively.

Example 13. Preparation of Ribociclib Succinate in Crystalline Form C (by the Disclosed Preparation Method of Ribociclib Succinate in Crystalline Form C, Using Isobutanol as the Organic Solvent, with Crystal Seeds)

A nitrogen-flushed 20-mL round bottom flask was charged with 0.57 g (1.05 eq) succinic acid and 16 mL isobutanol (iBuOH). The resulted solution was heated to 60±2° C., and stirred until the solids were fully dissolved, producing a clear solution. The heated succinic acid/iBuOH solution was then filtered through filter paper, and the filtrate was maintained at 40±5° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 74 mL isobutanol. The resulted solution was heated to 80±2° C. and stirred for 1 h, until complete dissolution was observed, producing a clear yellow solution. The yellow solution was cooled to 75±2° C., added with the prepared 40±5° C. of succinic acid/iBuOH solution over 4 min, and then maintained at 75±2° C. The solution was added 1% of ribociclib succinate in crystalline form B as crystal seed, and then an amount of solid was precipitated. After that, the mixed solution was heated to 78±2° C. and stirred for 1 h. Then the mixed solution was cooled to 20±2° C. and stirred for 1 h. A filter cake was subsequently obtained through suction filtration, rinsed with 5 mL and 5±2° C. of isopropanol, and then dried in the vacuum oven at 55±5° C. for 16 h. Approximately 2.3 g of ribociclib succinate in crystalline form C was obtained as pale yellow solids (approximately 90% molar recovery rate).

Example 14. Preparation of Ribociclib Succinate in Crystalline Form D (by the Disclosed Preparation Method of Ribociclib Succinate in Crystalline Form D, without Crystal Seeds)

Figure 8:
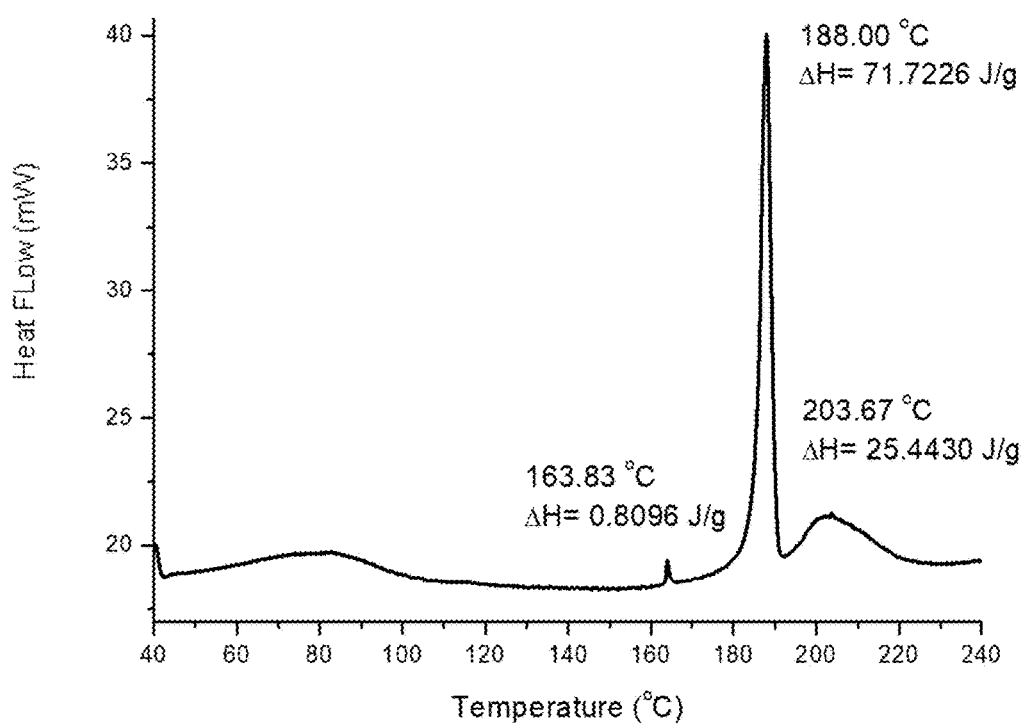
FIG. 8 is the DSC curve of the ribociclib succinate in crystalline form D of the present invention.
Figure 9:
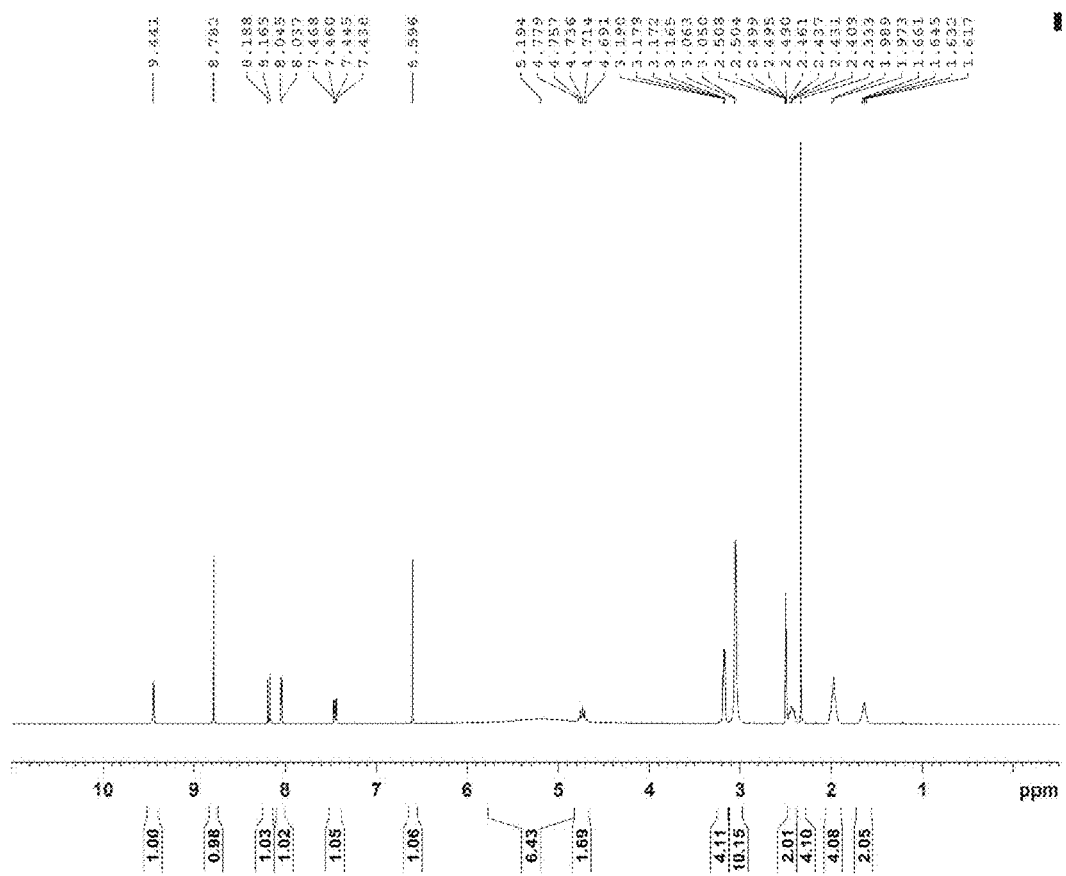
FIG. 9 is the nuclear magnetic hydrogen spectrum of the ribociclib succinate in crystalline form C of the present invention.

A nitrogen-flushed 20-mL round bottom flask was charged with 0.57 g (1.05 eq) of succinic acid and 11 mL methanol (MeOH). The resulted solution was heated to 65±2° C., and stirred until the solids were fully dissolved, producing a clear solution. The heated succinic acid/MeOH solution was then filtered through filter paper, and the filtrate was maintained at 60±5° C. A nitrogen-flushed 250-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2, 3-d]pyrimidine-6-carboxamide and 58 mL methanol. The resulted solution was heated to 65±2° C. and stirred for 1 h, until complete dissolution was observed, producing a clear yellow solution. The yellow solution was cooled to 59±2° C., added with the prepared 60±2° C. of succinic acid/MeOH solution over 5 min, and then maintained at 58±2° C. After that, the mixed solution was cooled to 54±3° C. and stirred for 1.3 h. Then the mixed solution was further cooled to 10±2° C. and stirred for 1 h. A filter cake was subsequently obtained through suction filtration, rinsed with 5 mL and 5±2° C. methanol, and then dried in the vacuum oven at 55±5° C. for 16 h. Approximately 2.312 g of ribociclib succinate in crystalline form D was obtained as yellow solids (approximately 91% molar recovery rate). The ribociclib succinate product had 99.8% purity, 5.0 wt % water, and 21.8 wt % succinic acid. FIG. 7, FIG. 8, and FIG. 9 show an XRPD pattern, a DSC curve, and a nuclear magnetic hydrogen spectrum of the product respectively.

Example 15. Preparation of Ribociclib Succinate in Crystalline Form D (by the Disclosed Preparation Method of Ribociclib Succinate in Crystalline Form D, with Crystal Seeds)

A nitrogen-flushed 20-mL round bottom flask was charged with 0.57 g (1.05 eq) succinic acid and 11 mL methanol (MeOH). The resulted solution was heated to 65±2° C., and stirred until the solids were fully dissolved, producing a clear solution. The heated succinic acid/MeOH was then filtered through filter paper, and the filtrate was maintained at 60±5° C. A nitrogen-flushed 100-mL three-neck flask was charged with 2.0 g (1.00 eq) of 7-cyclopentyl-N,N-dimethyl-2-{[5-(piperazin-1-yl)pyridin-2-yl]amino}-7H-pyrrolo[2, 3-d]pyrimidine-6-carboxamide and 58 mL methanol. The resulted solution was heated to 65±2°

C. and stirred for 1 h, until complete dissolution was observed, producing a clear yellow solution. The yellow solution was cooled to 58±2° C., added with the prepared 60±2° C. of succinic acid/MeOH solution over 5 min, and then maintained at 58±2° C. The solution was added 1% of ribociclib succinate in crystalline form B as crystal seed, and then an amount of solid was precipitated. After that, the mixed solution was cooled to 53±3° C. and stirred for 1 h. Then the mixed solution was further cooled to 10±2° C. and stirred for 1 h. A filter cake was subsequently obtained through suction filtration, rinsed with 5 mL and 5±2° C. of methanol, and then dried in the vacuum oven at 55±5° C. for 16 h. Approximately 2.301 g of ribociclib succinate in crystalline form D was obtained as yellow solids (approximately 90% molar recovery rate).

Example 16. Preparation of Ribociclib Succinate in Crystalline Form B (by the Disclosed Preparation Method of Ribociclib Succinate in Crystalline Form B (II), without Crystal Seeds)

Figure 13:
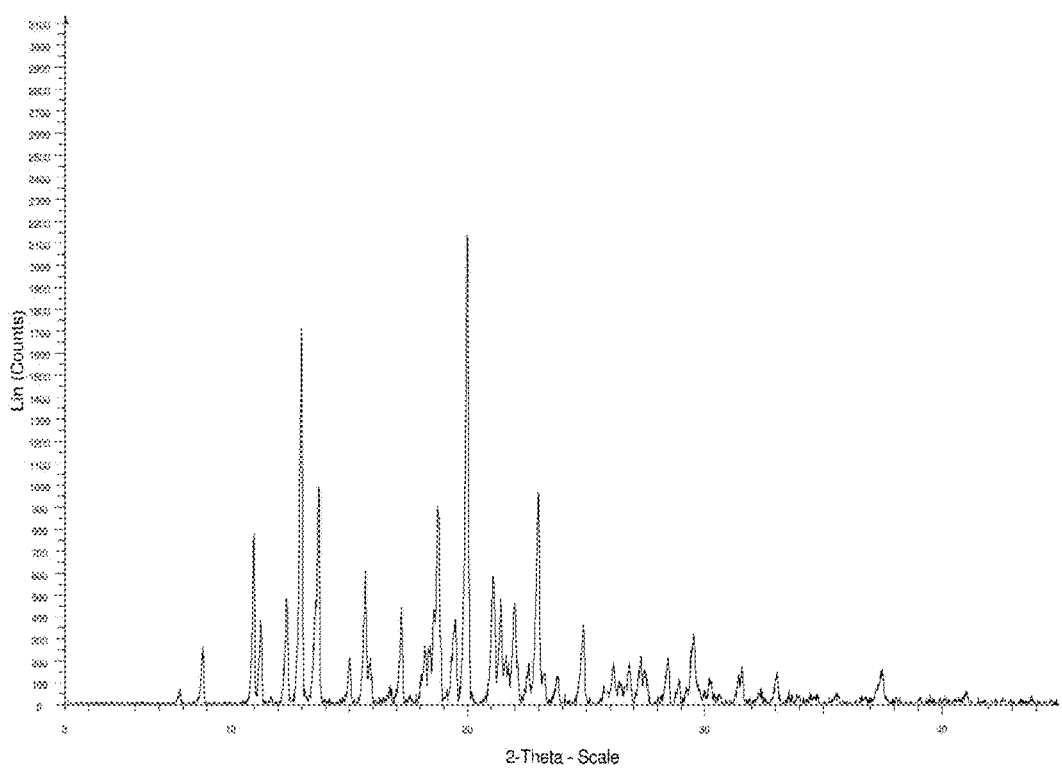
FIG. 13 is the XRPD pattern of the ribociclib succinate in crystalline form B that is transformed from the ribociclib succinate in crystalline form C of the present invention.

A nitrogen-flushed 250-mL three-neck flask was charged with 2.00 g ribociclib succinate in crystalline form C and 120 mL isopropanol (30 mM). The resulted solution was heated to 80±2° C. and stirred for 3 h. The solution was then cooled to 20±2° C. and stirred for 1 h. A filter cake was subsequently obtained through suction filtration, rinsed with 2 mL isopropanol, and then dried in the vacuum oven at 60° C. for 16 h. Approximately 1.88 g of ribociclib succinate in crystalline form B was obtained as off-white solids (approximately 94% molar recovery rate). FIG. 13 shows an XRPD pattern of the product.

Example 17. Preparation of Ribociclib Succinate in Crystalline Form B (by the Disclosed Preparation Method (II) of Ribociclib Succinate in Crystalline Form B, with Crystal Seeds)

A nitrogen-flushed 500-mL three-neck flask was charged with 6.00 g ribociclib succinate in crystalline form C and 310 mL isopropanol (35 mM). The resulted solution was heated to 80±2° C. and stirred for 3 h. The solution was added with 1% standard ribociclib succinate in crystalline form B as crystal seeds and stirred at 80±2° C. for 2 h. After that, the solution was cooled to 20±2° C. and stirred for 1 h. A filter cake was subsequently obtained through suction filtration, rinsed with 10 mL isopropanol, and then dried in the vacuum oven at 60° C. for 16 h. Approximately 5.81 g of ribociclib succinate in crystalline form B was obtained as off-white solids (approximately 96% molar recovery rate).

Example 18. Preparation of Ribociclib Succinate in Crystalline Form B (by the Disclosed Preparation Method of Ribociclib Succinate in Crystalline Form B (II), without Crystal Seeds)

Figure 14:
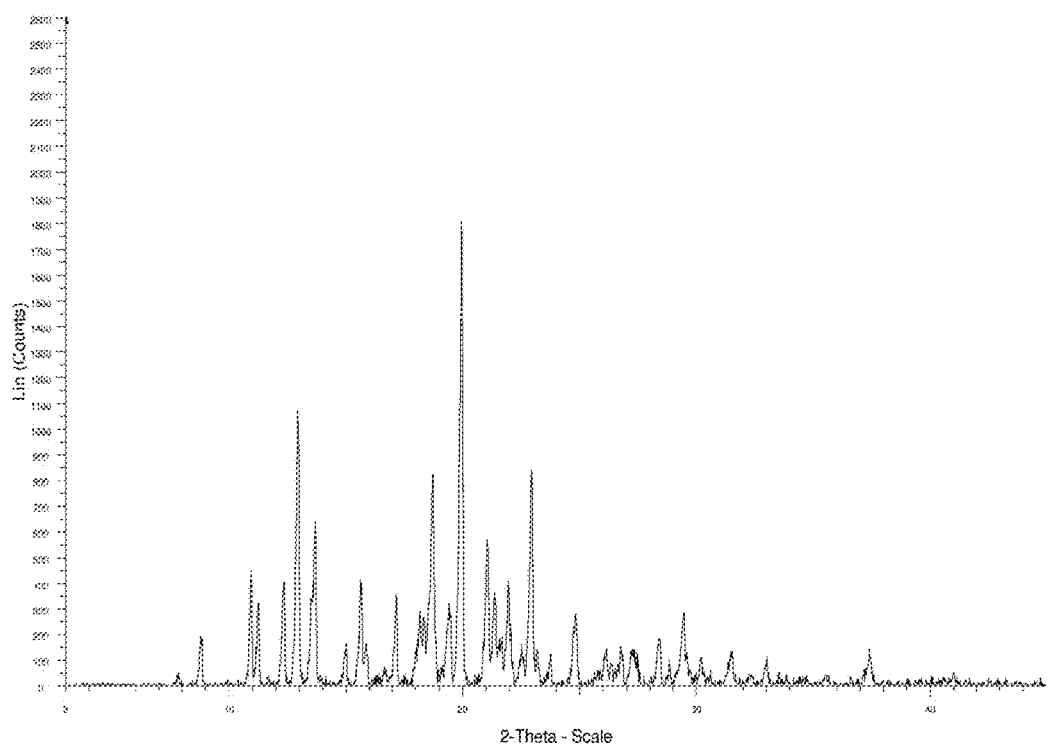
FIG. 14 is the XRPD pattern of the ribociclib succinate in crystalline form B that is transformed from the ribociclib succinate in crystalline form A of the present invention.

A nitrogen-flushed 250-mL three-neck flask was charged with 2.00 g ribociclib succinate in crystalline form A and 120 mL isopropanol (30 mM). The resulted solution was heated to 80±2° C. and stirred for 3 h. The solution was then cooled to 20±2° C. and stirred for 1 h. A filter cake was subsequently obtained through suction filtration, rinsed with 2 mL isopropanol, and then dried in the vacuum oven at 60° C. for 16 h. Approximately 1.88 g of ribociclib succinate in crystalline form B was obtained as off-white solids (approximately 94% molar recovery rate). FIG. 14 shows an XRPD pattern of the product.

Example 19. Preparation of Ribociclib Succinate in Crystalline Form B (by the Disclosed Preparation Method (II) of Ribociclib Succinate in Crystalline Form B, with Crystal Seeds)

A nitrogen-flushed 250-mL three-neck flask was charged with 2.00 g ribociclib succinate in crystalline form A and 120 mL isopropanol (30 mM). The resulted solution was heated to 80±2° C. and stirred for 1 h. The solution was added with 1% standard ribociclib succinate in crystalline form B as crystal seeds and stirred at 80±2° C. for 2 h. After that, the solution was cooled to 20±2° C. and stirred for 1 h. A filter cake was subsequently obtained through suction filtration, rinsed with 2 mL isopropanol, and then dried in the vacuum oven at 60° C. for 16 h. Approximately 1.89 g of ribociclib succinate in crystalline form B was obtained as off-white solids (approximately 94.6% molar recovery rate).

Example 20. Preparation of Crystalline Ribociclib Semi-Succinate

Figure 11:
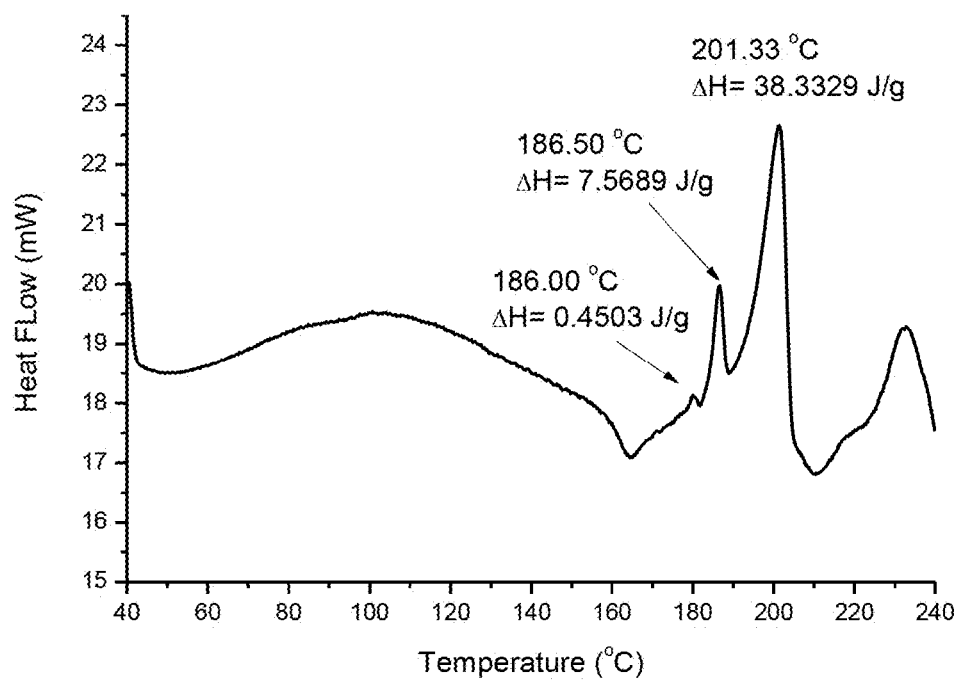
FIG. 11 is the DSC curve of the ribociclib semi-succinate of the present invention.
Figure 12:
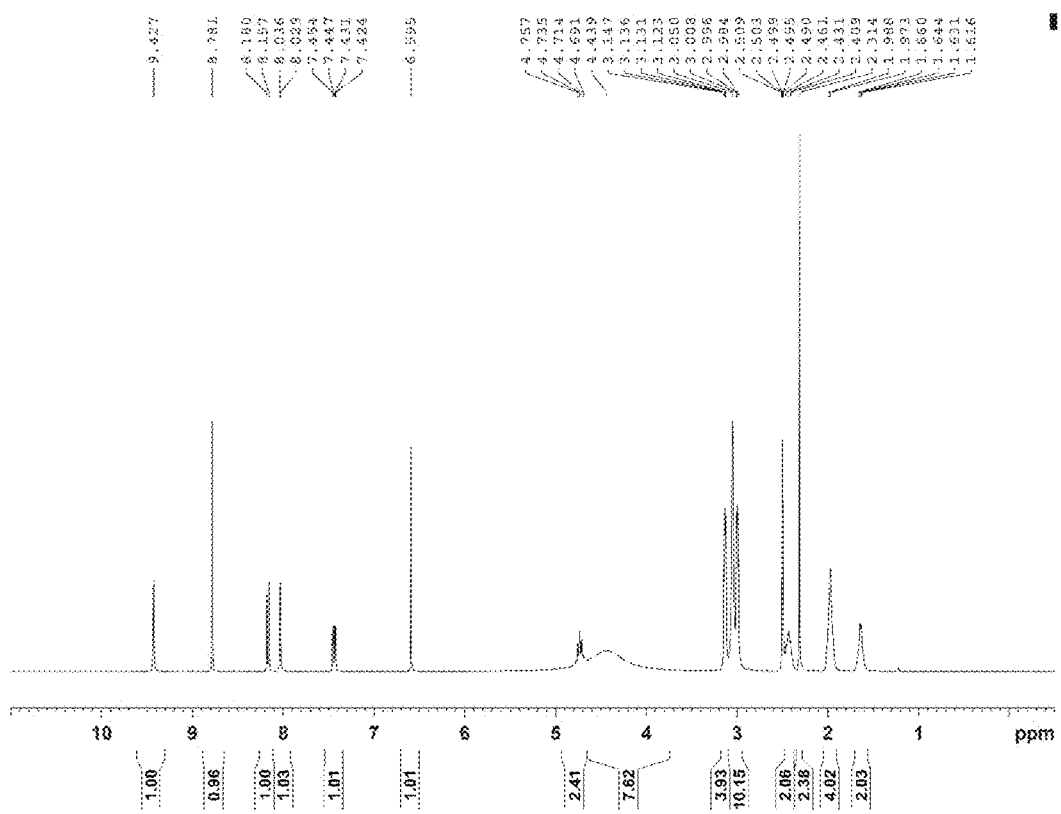
FIG. 12 is the nuclear magnetic hydrogen spectrum of the ribociclib semi-succinate of the present invention.

A nitrogen-flushed 50-mL three-neck flask was charged with 5.00 g ribociclib succinate in crystalline form B and 12.5 mL water. The resulted solution was stirred for 2 h under room temperature. A filter cake was then obtained through suction filtration, rinsed with 1 mL water, and then dried in the vacuum oven at 55±5° C. for 16 h. Approximately 1.35 grams of ribociclib semi-succinate was obtained as tawny solids (approximately 27% molar recovery rate). The ribociclib semi-succinate product had 99.8% purity, 5.5 wt % water, and 9.8 to 14.5 wt % succinic acid. FIG. 10, FIG. 11, and FIG. 12 show an XRPD pattern, a DSC curve, and a nuclear magnetic hydrogen spectrum of the product respectively.

Example 21. Preparation of Crystalline Ribociclib Semi-Succinate

A nitrogen-flushed 50-mL three-neck flask was charged with 1.00 g ribociclib succinate in crystalline form B, 34.6 mL isopropanol and 2.4 mL water. The resulted solution was heated to 80±2° C. and stirred for 1 h. The solution was cooled to 20±2° C. and stirred for 1 h. A filter cake was then obtained through suction filtration, and then dried in the vacuum oven at 45±5° C. for 16 h. Approximately 0.807 g of ribociclib semi-succinate was obtained as tawny solids (approximately 80.7% molar recovery rate).

Comparative Example: Preparation of Ribociclib Succinate in Crystalline Form a In the comparative example, ribociclib succinate in crystalline form A was prepared, and the prepared ribociclib succinate had the same crystalline structure as disclosed in WO 2012/064805A1.

Figure 15:
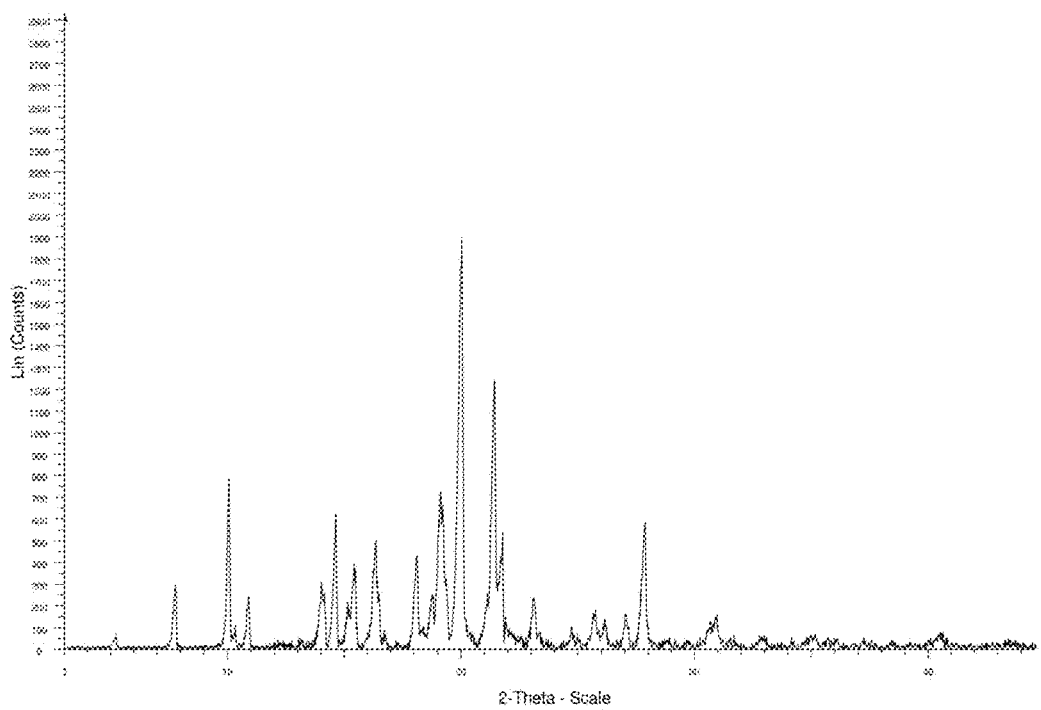
FIG. 15 is the XRPD pattern of the ribociclib succinate in crystalline form A in the comparative example of the present invention.
Figure 16:
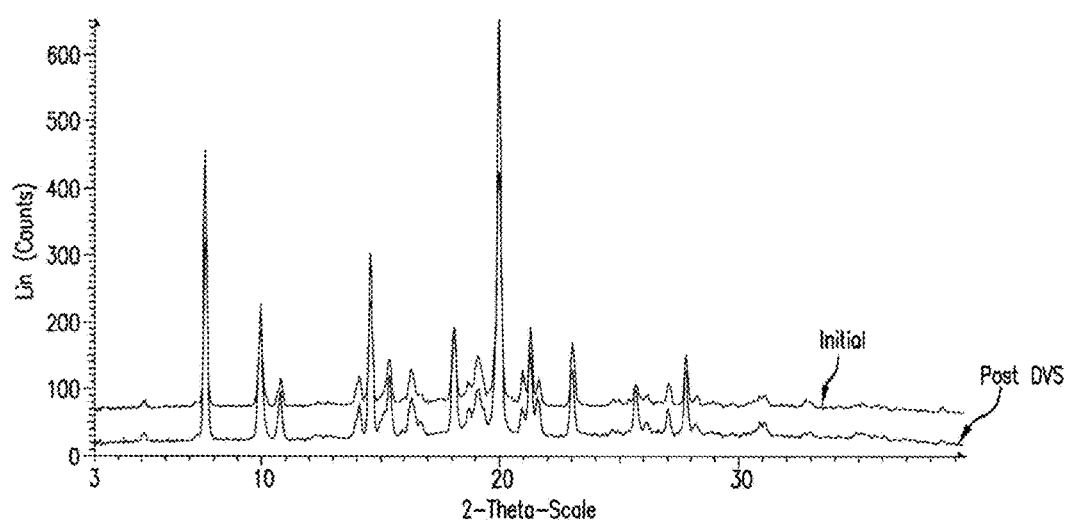
FIG. 16 is the XRPD pattern of FIG. 6 of the ribociclib succinate in WO 2012/064805A1.
Figure 17:
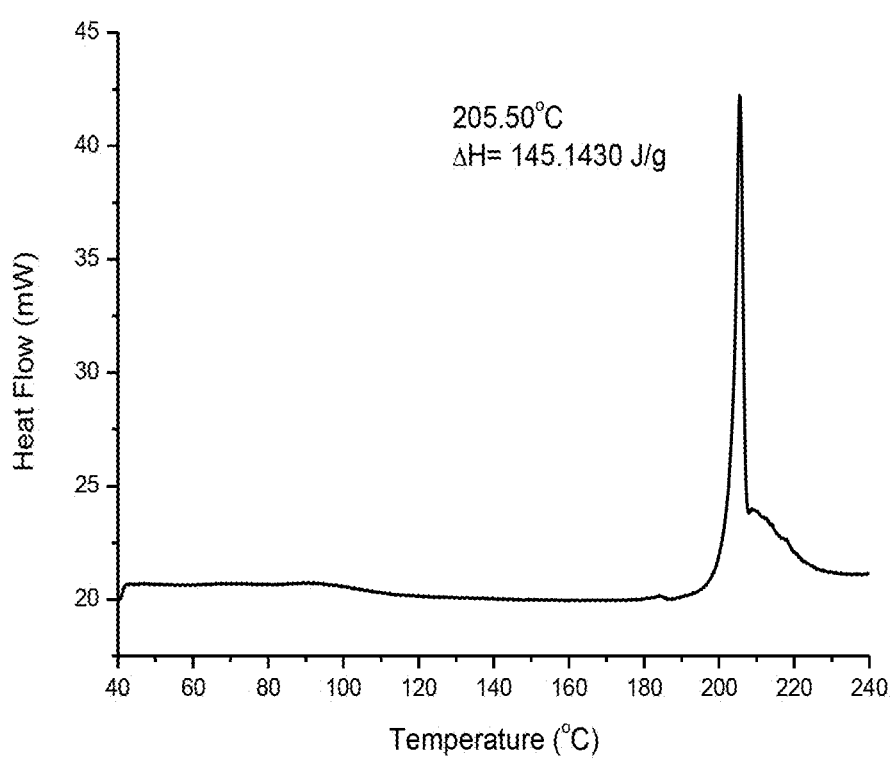
FIG. 17 is the DSC curve of the ribociclib succinate in crystalline form A in the comparative example of the present invention.

A nitrogen-flushed 250-mL round bottom flask was charged with 3.22 g succinic acid (1.05 eq) and 90.0 mL isopropanol (iPrOH). The resulted solution was heated to 60±2° C., and stirred until the solids were fully dissolved, producing a clear solution. The heated succinic acid/iPrOH solution was then filtered through filter paper, and the filtrate was maintained at 40±2° C. A nitrogen-flushed 1-L three-neck flask was charged with 11.3 g (1.00 eq) of 7-cyclopentyl-N,N-dimethyl-2-{[5-(piperazin-1-yl)pyridin-2-yl]amino}-7H-pyrrolo[2,3-d]pyrimidine-6-carboxamide and 410 mL isopropanol. The resulted solution was heated to 80±2° C. and stirred for 1 h, until complete dissolution was observed, producing a clear yellow solution. The yellow solution was cooled to 75±2° C., added with the prepared 40±2° C. succinic acid/iPrOH solution. About 80% of the succinic acid isopropanol solution was added within 3 min, during which time the mixed solution was maintained at 75±2° C. After that, 1% standard ribociclib succinate in crystalline form A was added as crystal seeds, followed by the remaining succinic acid solution. The mixed solution was heated to 80-2° C. and stirred for 1 h. Then the mixed solution was cooled to 20±2° C. and stirred for 1 h. A filter cake was subsequently obtained through suction filtration, rinsed with 10 mL isopropanol, and then dried in the vacuum oven at 60° C. for 16 h. Approximately 13.6 g of ribociclib succinate in crystalline form A was obtained as yellow solids (approximately 95% molar recovery rate). The ribociclib succinate product had 99.7% purity, 0.69 wt % water, and 21.7 wt % succinic acid. FIG. 15 and FIG. 17 show an XRPD pattern and a DSC curve of the product respectively. By comparing FIG. 15 with FIG. 16 (i.e. the XRPD pattern of FIG. 6 of the ribociclib succinate in WO 2012/064805A1), the crystalline structure of the crystalline-form-A ribociclib succinate in the comparative example is the same as the crystalline structure of the ribociclib succinate in WO 2012/064805A1.

In view of the XRPD patterns of ribociclib succinates in crystalline forms B, C, and D and ribociclib semi-succinate of Examples 2, 12, 14 and 16, the ribociclib succinate in crystalline form A of the comparative example, and the XRPD pattern of FIG. 6 of the ribociclib succinate in WO 2012/064805A1, the XRPD pattern of the ribociclib succinate in crystalline form B of example 2, as FIG. 1 shown, has characteristic peaks at 2θ values of 12.9°±0.20°, 13.7°±0.20°, 18.7°±0.20°, 19.9°±0.20°, and 23.0°±0.20° and secondary characteristic peaks (of lower intensities than the characteristic peaks) at 2θ values of 8.8°±0.20°, 15.4°±0.20°, 17.2°±0.20°, and 24.8°±0.20°. Referring to FIG. 4, the XRPD pattern of the ribociclib succinate in crystalline form C of example 12 has characteristic peaks at 2θ values of 10.0°±0.20°, 20.0°±0.20°, 21.4°±0.20°, 23.0°±0.20°, and 27.9°±0.20° and a secondary characteristic peak (of lower intensity than the characteristic peaks) at the 2θ value of 7.7°±0.20°. Referring to FIG. 7, the XRPD pattern of the ribociclib succinate in crystalline form D of example 14 has characteristic peaks at 2θ values of 13.2°±0.20°, 18.1°±0.20°, 20.1°±0.20°, and 21.7°±0.20° and secondary characteristic peaks (of lower intensities than the characteristic peaks) at 2θ values of 10.7°±0.20° and 16.0°±0.20°. Referring to FIG. 10, the XRPD pattern of the crystalline ribociclib semi-succinate of example 16 has characteristic peaks at 2θ values of 13.0°±0.20°, 16.2°±0.20°, 18.5°±0.20°, 20.1°±0.20°, 21.6°±0.20°, and 22.1°±0.20° and secondary characteristic peaks (of lower intensities than the characteristic peaks) at 2θ values of 10.7°±0.20°, 14.2°±0.20°, 17.8°±0.20°, and 26.2°±0.20°. Referring to FIGS. 15 and 16, both the XRPD pattern of the ribociclib succinate in crystalline form A of the comparative example and the ribociclib succinate XRPD pattern in FIG. 6 of WO 2012/064805A1 have characteristic peaks at 2θ values of 7.8°±0.20°, 10.0°±0.20°, 14.5°±0.20°, 20.0°±0.20°, and 21.5°±0.20°.

According to the above, the crystalline structures of the ribociclib succinates in crystalline forms B, C, and D prepared according to the present invention and of the ribociclib semi-succinate prepared according to the present invention are significantly different from that of the ribociclib succinate in crystalline form A of the comparative example and of the ribociclib succinate disclosed in WO 2012/064805A1. This indicates that the former ribociclib succinates/semi-succinate and the latter ribociclib succinates are in different crystalline forms.

Testing Example

The ribociclib succinate in crystalline form A of the comparative example and the ribociclib succinate in crystalline form B of example 2 were transferred into a constant temperature and humidity chamber, where the ribociclib succinate powders were each exposed to a 25° C./75% RH environment and an 80° C./75% RH environment to have their crystalline stability determined. The results are shown in Table 1 and Table 2.

As shown in Table 1, the ribociclib succinate in crystalline form A maintained its crystalline form under 25° C./75% RH and transformed from crystalline form A to crystalline form B under 80° C./75% RH.

TABLE 1

| Ribociclib succinate in crystalline form A of comparative example | | |
|---|---|---|
| | 25° C., 75%RH | 80° C., 75%RH |
| 1 day | Stayed as A | Transformed from A to B |
| 3 days | Stayed as A | Transformed from A to B |
| 7 days | Stayed as A | Transformed from A to B |

As shown in Table 2, the ribociclib succinate in crystalline form B maintained its crystalline form and did not transform to other crystalline forms under 80° C./75% RH as well as 25° C./75% RH.

TABLE 2

| Ribociclib succinate in crystalline form B of Example 2 | | |
|---|---|---|
| | 25° C., 75%RH | 80° C., 75%RH |
| 1 day | Stayed as B | Stayed as B |
| 3 days | Stayed as B | Stayed as B |
| 7 days | Stayed as B | Stayed as B |

The testing example shows that the ribociclib succinate in crystalline form B prepared according to the present invention stored well and is therefore suitable for industrial use.

As above, the present invention uses lithium bis(trimethylsilyl)amine rather than the costly palladium acetate (Pd(OAc)$_2$) in preparing ribociclib succinates in crystalline forms B, C, and D so that production costs can be lowered. In addition, to reduce the residue of toxic organic solvents, a low-toxicity and highly volatile solvent such as ethanol or isopropanol is used to prepare ribociclib succinates in crystalline forms B and C. Moreover, the ribociclib succinate in crystalline form B prepared according to the present invention is stable in storage and insusceptible to degradation of its crystalline form as may otherwise result from changes in temperature or humidity. Thus, the present invention provides ribociclib succinates in crystalline forms B, C, and D and ribociclib semi-succinate salts suitable for industrial production and for use as therapeutic pharmaceutical compositions.

The above is the detailed description of the present invention. However, the above is merely the preferred Example of the present invention and cannot be the limitation to the implement scope of the present invention, which means the variation and modification according the present invention may still fall into the scope of the invention.

What is claimed is:

1. A crystalline form B of ribociclib succinate having a characteristic X-ray powder diffraction pattern comprising peaks at 2θ values of 12.9°±0.20°, 13.7°±0.20°, 18.7°±0.20°, 19.9°±0.20° and 23.0°±0.20.

2. The crystalline form B of ribociclib succinate of claim 1, wherein the X-ray powder diffraction pattern is the same as shown in FIG. 1.

3. A pharmaceutical composition comprising at least one pharmaceutically acceptable vehicle, diluent and/or excipient and a crystalline form B of ribociclib succinate having a characteristic X-ray powder diffraction pattern comprising peaks at 2θ values of 12.9°±0.20°, 13.7°±0.20°, 18.7°±0.20°, 19.9°±0.20° and 23.0°±0.20°.

4. A method for preparing a crystalline form B of ribociclib succinate having a characteristic X-ray powder diffraction pattern comprising peaks at 2θ values of 12.9°±0.20°, 13.7°±0.20°, 18.7°±0.20°, 19.9°±0.20° and 23.0°±0.20°, wherein the method comprises the following steps:

(i) dissolving a crystalline form C of ribociclib succinate having a characteristic X-ray powder diffraction pattern comprising peaks at 2θ values of 10.0°±0.20°, 20.0°±0.20°, 21.4°±0.20°, 23.0°±0.20° and 27.9°±0.20° in isopropanol under a nitrogen atmosphere;

(ii) heating the solution formed in step (i) to a temperature in the range of 78° C. to 82° C.;

(iii) stirring the solution of step (ii) for three hours;

(iv) cooling the solution of step (iii) to a temperature in the range of 18° C. to 22° C.;

(v) stirring the solution of step (iv) for one hour; and (vi) obtaining the crystalline form B of ribociclib succinate.

5. The method of claim 4, wherein the crystalline form C of ribociclib succinate has a characteristic X-ray powder diffraction pattern the same as shown in FIG. 4.

* * * * *